US012797248B2

(12) United States Patent
Herfort et al.

(10) Patent No.: US 12,797,248 B2
(45) Date of Patent: Nov. 17, 2026

(54) SYSTEMS AND METHODS FOR SOUND PROCESSING IN PERSONAL PROTECTIVE EQUIPMENT

(71) Applicant: 3M INNOVATIVE PROPERTIES COMPANY, St. Paul, MN (US)

(72) Inventors: Frank T. Herfort, Korschenbroich (DE); Jan D. Forster, Aachen (DE); Torsten Koppenhagen, Neuss (DE); Vijay K. Gidla, Värnamo (SE); Abel Gladstone Mangam, Värnamo (SE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 308 days.

(21) Appl. No.: 18/558,548

(22) PCT Filed: Apr. 25, 2022

(86) PCT No.: PCT/IB2022/053811

§ 371 (c)(1),
(2) Date: Nov. 2, 2023

(87) PCT Pub. No.: WO2022/234384

PCT Pub. Date: Nov. 10, 2022

(65) Prior Publication Data

US 2024/0216179 A1 Jul. 4, 2024

Related U.S. Application Data

(60) Provisional application No. 63/201,539, filed on May 4, 2021.

(51) Int. Cl.
*A61F 9/06* (2006.01)
*A61F 11/14* (2006.01)
(Continued)

(52) U.S. Cl.
CPC .............. *A61F 11/145* (2022.01); *A61F 9/06* (2013.01); *G06F 3/165* (2013.01); *H04R 1/1041* (2013.01);
(Continued)

(58) Field of Classification Search
CPC .......... A61F 11/145; A61F 9/06; G06F 3/165; H04R 1/1041; H04R 1/1083
(Continued)

(56) References Cited

U.S. PATENT DOCUMENTS 6,868,378 B1 3/2005 Breton
9,716,939 B2 7/2017 Di Censo et al.
(Continued)

FOREIGN PATENT DOCUMENTS

EP 3214857 A1 * 9/2017 ......... A61N 1/36038
WO 2013177285 A1 11/2013
WO 2021064658 A1 4/2021

OTHER PUBLICATIONS

Hershey, "CNN Architectures for Large-Scale Audio Classification", IEEE International Conference on Acoustics, Speech and Signal Processing (ICASSP), 2017, pp. 131-135.
(Continued)

*Primary Examiner* — Carolyn R Edwards
*Assistant Examiner* — Friedrich Fahnert

(57) ABSTRACT

A personal protective equipment device is presented that includes a speaker configured to provide a modified sound to a user. The device also includes a microphone configured to capture an ambient sound stream. The device also includes a sound analyzer that receives the ambient sound stream from the microphone and identifies a first sound in the ambient sound. The device also includes a sound processor that applies a model to the first sound, based on the sound identification, to obtain the modified sound, wherein the
(Continued)

model changes a characteristic of the identified sound. The modified sound is provided to the speaker. The model comprises an algorithm stored locally in a model database within a memory of the personal protective equipment device.

20 Claims, 15 Drawing Sheets

(51) Int. Cl.
*G06F 3/16* (2006.01)
*H04R 1/10* (2026.01)

(52) U.S. Cl.
CPC ..... *H04R 1/1083* (2013.01); *H04R 2201/107* (2013.01); *H04R 2460/01* (2013.01)

(58) Field of Classification Search
USPC ............................................................ 381/72
See application file for complete search history.

(56) References Cited

U.S. PATENT DOCUMENTS

| | | | |
|---|---|---|---|
| 10,045,115 | B2 | 8/2018 | Klimanis et al. |
| 2008/0240458 | A1* | 10/2008 | Goldstein ............ H04R 1/1083 381/72 |
| 2015/0222977 | A1 | 8/2015 | Angel, Jr. |
| 2016/0269841 | A1 | 9/2016 | Shinde |
| 2018/0184195 | A1 | 6/2018 | Boesen |
| 2019/0053950 | A1 | 2/2019 | Muggleton |
| 2019/0130926 | A1* | 5/2019 | Giri ......................... G10L 17/02 |
| 2019/0196777 | A1 | 6/2019 | Kovacevic |
| 2020/0030151 | A1* | 1/2020 | Hemberg ................ A61F 11/14 |

OTHER PUBLICATIONS

International Search Report for PCT International Application No. PCT/IB2022/053811, mailed on Aug. 18, 2022, 5 pages.

* cited by examiner

SYSTEMS AND METHODS FOR SOUND PROCESSING IN PERSONAL PROTECTIVE EQUIPMENT

CROSS REFERENCE TO RELATED APPLICATIONS

This application is a national stage filing under 35 U.S.C. 371 of PCT/IB2022/053811, filed Apr. 25, 2022, which claims the benefit of U.S. Provisional Application No. 63/201,539, filed May 4, 2021, the disclosure of which is incorporated by reference in its/their entirety herein.

BACKGROUND

Maintaining the safety and health of workers is a major concern across many industries. Various rules and regulations have been developed to aid in addressing this concern. Such rules provide sets of requirements to ensure proper administration of personnel health and safety procedures. To help in maintaining worker safety and health, some individuals may be required to don, wear, carry, or otherwise use a personal protective equipment (PPE) article, if the individuals enter or remain in work environments that have hazardous or potentially hazardous conditions.

Consistent with evolving rules and regulations related to safety, safety is an important concern in any workplace requiring the use of PPE. Companies or businesses employing workers wearing articles of PPE also want to ensure that workers are complying with relevant laws, regulations and company policies related to proper use and maintenance of PPE.

SUMMARY

A personal protective equipment device is presented that includes a speaker configured to provide a modified sound to a user. The PPE device also includes a microphone configured to capture an ambient sound. The PPE device also includes a sound analyzer that receives the ambient sound from the microphone, parses it into a plurality of sound portions, compares the sound portions to a database of sound objects and, based on the comparison, identifies a first sound in the ambient sound. The PPE device also includes a sound processor that applies a model to the first sound, based on the sound identification, to obtain the modified sound, wherein the model changes a feature of the identified first sound. The modified sound is provided to the speaker. The model comprises an algorithm stored locally in a model database within a memory of the personal protective equipment device. The model database comprises a plurality of models, and wherein the plurality of models comprises a downloaded model.

Systems and methods herein provide an improved audio experience for a user, allowing for the amplification of sounds desirable or useful (such as acoustic warning signals including emergency notifications) for a user, reducing sounds that may be undesirable or damaging, and/or removing unwanted sounds altogether. Systems and methods herein provide an improved, customizable audio experience for users.

The details of one or more examples of the disclosure are set forth in the accompanying drawings and the description below. Other features, objects, and advantages of the disclosure will be apparent from the description and drawings, and from the claims.

DETAILED DESCRIPTION

Many types of personal protective equipment (PPE) include a speaker, a microphone, or both. The speakers may provide a received audio transmission to a user, while the microphones may capture audio from the wearer. Different forms of PPE have different quality microphones and speakers. Additionally, wearing different PPE interferes with the ability of microphones to pick up audio, and for speakers to transmit audio.

Some hearing protection devices include active hearing protection, which includes one or more microphones that receive ambient sound from a user's surroundings, a processor to process the sound to a safe level, and one or more speakers to play it back, at the safe level, to a user. Active hearing protection devices use electronic circuitry to pick up ambient sound through the microphone and convert them to safe levels before playing it back to the user through a speaker. Additionally, active hearing protection may comprise filtering out sound above a given sound pressure level, for example actively reducing the sound of a gunshot while providing human speech at substantially unchanged levels. At least some embodiments herein are applicable to active hearing devices.

In an active hearing protection system, a sound signal is first received by a microphone. The received sound signal is converted to an electronic signal for processing. After processing the sound signal such that all frequencies are at safe levels for a user, the sound signal is reproduced and played back to a user through a speaker of the hearing protection device.

Some active hearing protection units are level dependent, such that an electronic circuit adapts the sound pressure level. Level dependent hearing protection units help to filter out impulse noises, such as gunshots from surrounding noises, and/or continuously adapt all ambient sound received to an appropriate level before it is reproduced to a user. Active hearing protection units, specifically level dependent active hearing protection units, may be necessary to facilitate communication in noisy environments, or environments where noise levels can vary significantly, or where high impulse sounds may cause hearing damage. A user may need to hear nearby ambient sounds, such as machine sounds or speech, while also being protected from harmful noise levels.

Figure 1:
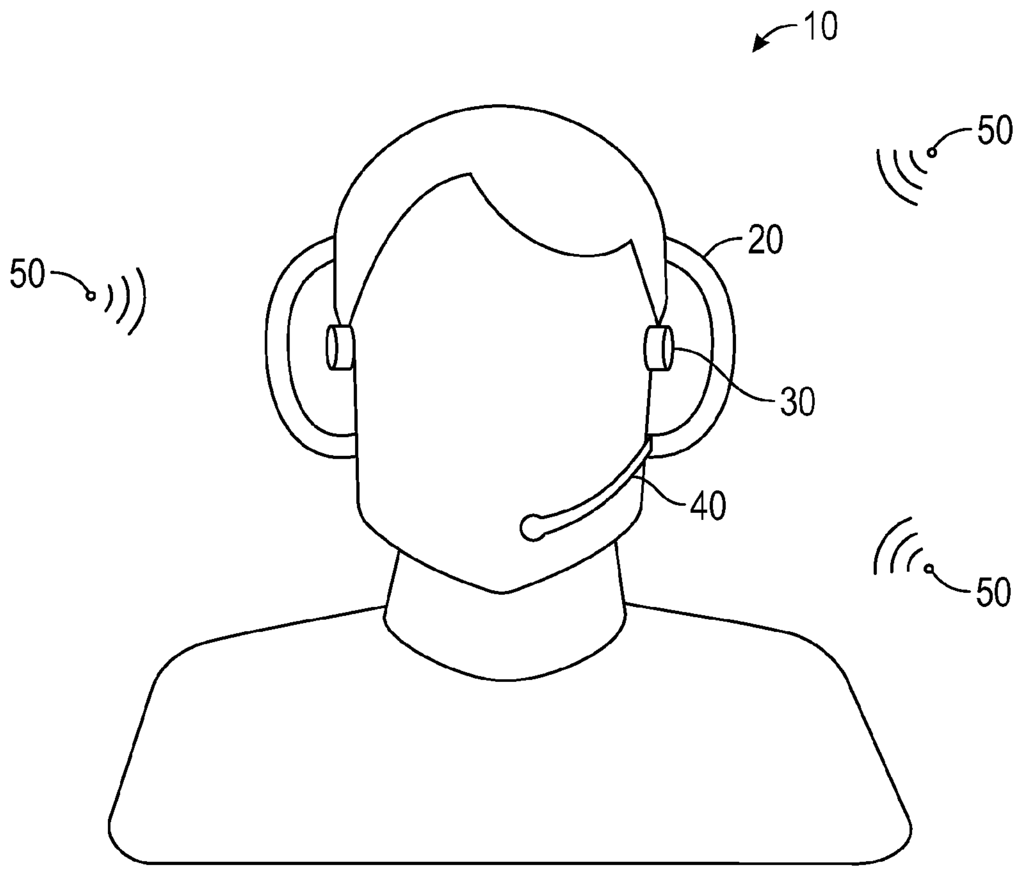
FIG. 1 illustrates a user of a hearing protection device.

As illustrated in FIG. 1, active hearing protection units can be provided using either ear plugs or ear-muff designs, or in a dual protection mode, as described in U.S. Provisional Patent Application with Ser. No. 62/909,989, filed Oct. 3, 2019, which is herein incorporated by reference.

However, while active hearing protection is capable of reducing sound of essentially all frequencies to a safe level, it does not selectively reduce or filter out individual sound components to obtain both an improved hearing experience of ambient sound above or below safe level and a safe overall sound level played back to the wearer. In many environments, it may be helpful to selectively reduce sounds. For example, while in a battlefield scenario, it may be desired for a PPE to selectively reduce the sound of gunshots and selectively amplify the sound of human speech. In a construction scenario, it may be helpful to selectively reduce the sound of chainsaws or other power tools and amplify a sound indicating a passing ambulance or heavy machinery moving toward the wearer.

A system is desired that can recognize individual sounds within an incoming sound stream and apply one or more models to the recognized sounds to change a perception of those sounds to a user. As used herein, applying a model refers to applying an algorithm to the detected sound frequency or frequencies, changing an auditory experience of a user. The algorithm may amplify, reduce, cancel, add an overlay to, or otherwise alter the incoming sound to provide a modified sound, which is then broadcast to a user. For example, an incoming sound stream may include a chainsaw sawing, a supervisor speaking, and a beeping sound indicative of heavy machinery backing up near the user. Applying a model may include any, or all of, reducing the sound of the chainsaw, amplifying the speech of the supervisor, canceling the beeping sound while providing an auditory alert warning of the nearby heavy machinery.

It is known in the prior art that a sound can be recognized and an alert provided thereabout, for example as described in U.S. PAP 2015/0222977, published on Aug. 6, 2015. Additionally, it is known in the prior art that a device can match a received sound to a registered sound pattern to generate an alert, as described in U.S. PAP 2016/0269841, published on Sep. 15, 2016. However, it has not previously been known to recognize a sound within a received sound stream, alter the sound, alter individual sound components, and recombine it into a broadcast sound to a wearer of a PPE device in substantially real-time.

FIG. 1 illustrates a dual hearing protection system in accordance with an embodiment of the present invention. However, while a dual hearing system 10 is illustrated, it is expressly contemplated that embodiments herein could include either earmuffs 20 or inner ear plugs 30, operating alone. A person 10 may be in an environment with a plurality of sounds 50. As illustrated in FIG. 1, different sounds 50 may have different sound pressure levels associated with them. Some of sounds 50 may be sounds that user 10 wants to hear, and may want amplified. Some other sounds 50 may be sounds that could distract a user 10, which a user may want reduced or cancelled altogether.

A dual hearing protection system can also include one or more microphones 40. Microphone 40 is illustrated in FIG. 1 as positioned to pick up the voice of user 10. However, other microphones (not shown) may be positioned to pick up ambient sounds 50. Additionally, each of first and second hearing protection systems 20, 30 may have one or more microphones 40.

Figure 2:
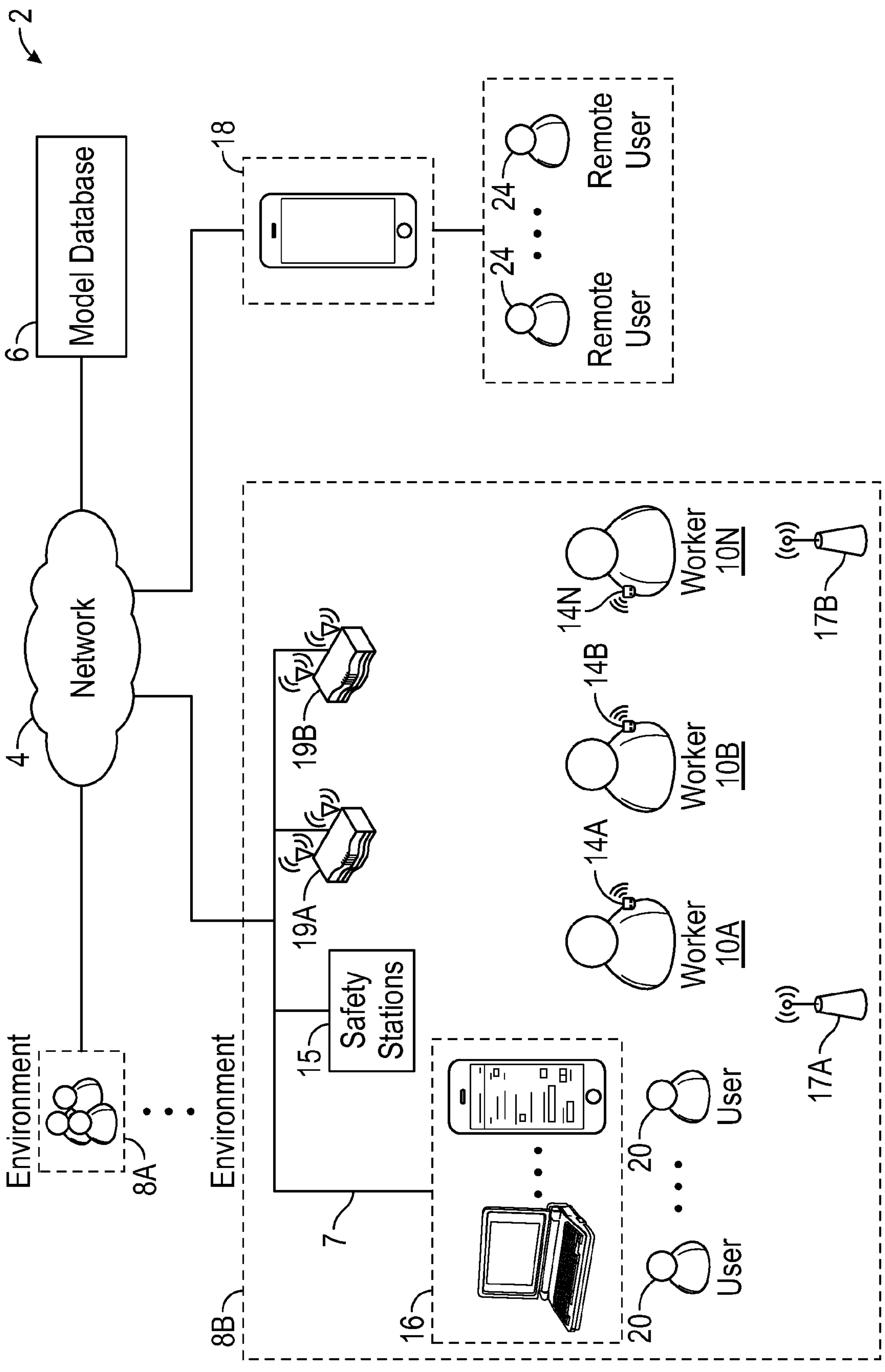
FIG. 2 illustrates a worksite in which embodiments of the present invention may be useful.

FIG. 2 illustrates a worksite in which embodiments of the present invention may be useful. FIG. 2 is a block diagram illustrating an example networked environment 2 for a worksite 8A or 8B. The worksite environments 8A and 8B may have one or more workers 10A-10N, each of which may be wearing different PPE, including hearing protection such as in-ear or over-hear protection described with respect to FIG. 1. Workers 10A-10N may all be in the same environment 2, but they may each be performing a variety of tasks. For each worker 10A-10N, different sound processing needs are required. For example, a worker operating a chainsaw may want the sound of a chainsaw reduced. But a passerby may want the sound amplified, or an alert provided that dangerous machinery is being operated nearby.

Environment 2 includes a model database 6 which includes models that may be accessed by PPE worn by users 10A-10N or may be downloaded into the PPE devices. For example, as described herein, individual models may be associated with sounds and may be accessed by a processor of a PPE device when a given sound is detected, so that the model can be applied. The models may be accessible from a local storage, within a PPE device, or may be downloaded from/accessible from a remote storage source, such as an online database.

Each of physical environments 8A and 8B represents a physical environment, such as a work environment, in which one or more individuals, such as workers 10, utilize personal protection equipment while engaging in tasks or activities within the respective environment.

In this example, environment 8A is shown as generally as having workers 10, while environment 8B is shown in expanded form to provide a more detailed example. In the example of FIG. 2, a plurality of workers 10A-10N may be wearing a variety of different PPE, such as ear muff hearing protectors, in-ear hearing protectors, hard hats, gloves, glasses, goggles, masks, respirators, hairnets, scrubs, or any other suitable personal protective equipment.

While an environment 2 is illustrated as a plant or industrial environment, it is also expressly contemplated that, in some embodiments, a model database may be accessible to a single user, with a single PPE device, such as a handyman operating a power tool alone during a home remodel project.

In general, model database 6, as described in greater detail herein, is configured to house models available for download by PPE within environments 8A and 8B. The models may be generated by manufacturers of the PPE, manufactures of devices (e.g. manufacturers of power tools), other third parties, or individuals who create and upload their own models to database 6. Database 6 may be accessed, through network 4, to one or more devices or displays 16 within an environment, or devices or displays 18, remote from an environment. For example, devices 16, 18 may have an application interface that allows a user 10A-10N to select models from database 6 for download to a PPE device. Additionally, the interface may also allow a user 10A-10N to upload a sound to database 6, and create or select a model for application to said sound. The user 10A-10N may then be able to download the created/selected model to a PPE device such that the model can be applied when the sound is detected in the future. In some embodiments, PPE devices do not have the ability to download models directly from database 6. In other embodiments, PPE devices can access database 6 to download models or upload sounds directly. For example, if a sound is received that is not recognized by a given PPE device, it may provide the sound to model database 6 for recognition. Model database 6 may have a greater database of recognizable sounds and may be able to provide a model that can be applied by the PPE to the sound. Said model may be automatically provided to a PPE through network 4, in one embodiment. In another embodiment, PPE may receive new models through a device 16, 18.

In some embodiments herein, an article of PPE may include one or more of embedded sensors, communication components, monitoring devices and processing electronics. In addition, each article of PPE may include one or more output devices for outputting data that is indicative of operation of the PPE and/or generating and outputting communications to the respective worker 10. For example, PPE may include one or more devices to generate audible feedback (e.g., one or more speakers), visual feedback (e.g., one or more displays, light emitting diodes (LEDs) or the like), or tactile feedback (e.g., a device that vibrates or provides other haptic feedback). Additionally, many types of PPE may include hearing protection devices capable of receiving sounds, applying models to the received sounds and outputting the process sounds.

In some examples, each of environments 8 include computing facilities, such as displays 16, or through associated PPEs, by which workers 10 can communicate with model database 6. For examples, environments 8 may be configured with wireless technology, such as 802.11 wireless networks, Bluetooth® networks, 802.15 ZigBee networks, and the like. In the example of FIG. 2, environment 8B includes a local network 7 that provides a packet-based transport medium for communicating with PPE computing system 6 via network 4. In addition, environment 8B includes a plurality of wireless access points 19A, 19B that may be geographically distributed throughout the environment to provide support for wireless communications throughout the work environment.

As shown in the example of FIG. 2, an environment, such as environment 8B, may also include one or more wireless-enabled beacons, such as beacons 17A-17C, that provide accurate location information within the work environment. For example, beacons 17A-17C may be GPS-enabled such that a controller within the respective beacon may be able to precisely determine the position of the respective beacon. Based on wireless communications with one or more of beacons 17, or data hub 14 worn by a worker 10 is configured to determine the location of the worker within work environment 8B. In this way, event data may be stamped with positional information.

In example implementations, an environment, such as environment 8B, may also include one or more safety stations 15 distributed throughout the environment. Safety stations 15 may allow one of workers 10 to check out articles of PPE and/or other safety equipment, verify that safety equipment is appropriate for a particular one of environments 8, and/or exchange data. For example, safety stations 15 may transmit alert rules, software updates, or firmware updates to articles of PPE or other equipment.

In addition, each of environments 8 include computing facilities that provide an operating environment for end-user computing devices 16 for interacting with model database 6 via network 4. For example, each of environments 8 typically includes one or more safety managers or supervisors, represented by users 20 or remote users 24, are responsible for overseeing safety compliance within the environment. For example, the end-user computing devices 16, 18 may be laptops, desktop computers, mobile devices such as tablets or so-called smart cellular phones.

As illustrated in FIG. 2, worksite 8B may have one or more cameras 60, either fixed within the worksite, mobile (e.g. drone, robot or equipment-mounted) or associated with a worker 10A-10N (e.g. an augmented reality headset or other camera worn in association with PPE, etc.).

Systems and methods herein allow for each PPE device to customize and improve an experience of each worker 10A-10N. Each worker, by downloading the necessary models from model database 6, can have a tailored auditory experience that amplifies desired sounds, reduces or cancels unwanted sounds, adds alert overlays, all based on recognizing incoming sounds within a stream of sounds entering a microphone of a PPE device worn by the worker.

Figure 3:
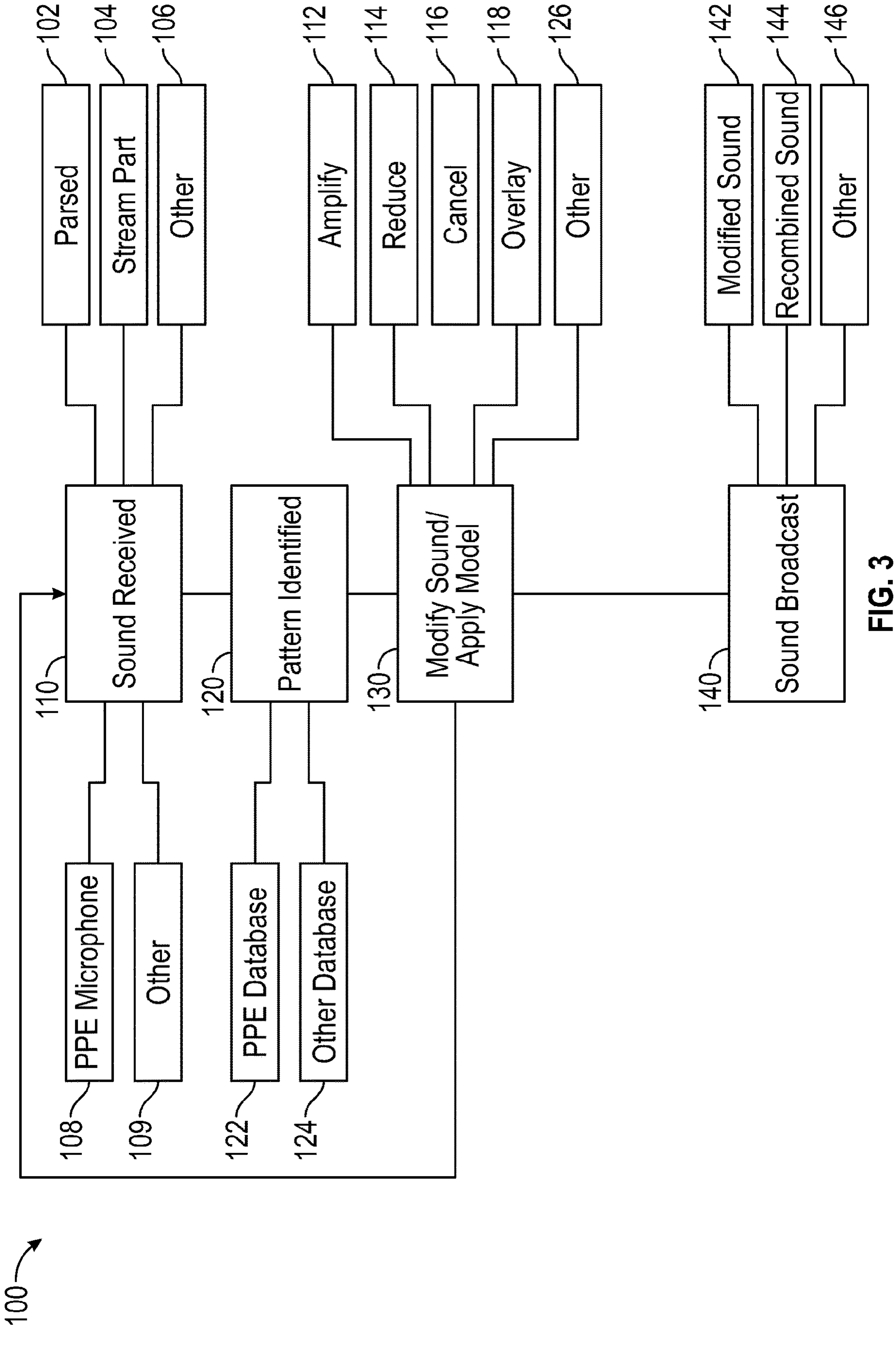
FIG. 3 illustrates a method of modifying a captured sound in an embodiment of the present invention.

FIG. 3 illustrates a method of modifying a captured sound in an embodiment of the present invention. Method 100 may be implemented in a hearing protection device, or other PPE with active hearing protection, to selectively adjust sounds within an incoming sound stream. First a sound is received, as indicated in block 110. Sound may be received through a microphone associated with the same PPE device that performs method 100, for example a microphone on an exterior of a headset. Or, in another embodiment, sound may be received through another mechanism, as indicated in block 109. For example, a human voice may be received by an antenna, broadcast from another source.

The sound received in block 110 may be received as part of a sound stream, as indicated in block 104. A processor associated with the PPE device may be responsible for parsing the sound from an incoming sound stream, or it may be received from another source that parsed it from a sound stream, as indicated in block 102. Other configurations are also envisioned, as indicated in block 106.

In block 120, a sound pattern is identified, for example by comparing the parsed sound to a database of sounds stored locally in the PPE device, as indicated in block 122, or stored remotely from the PPE device, as indicated in block 124. In some embodiments, the sound pattern is identified using machine learning or artificial intelligence, such as a model that is trained to detect the presence of certain sounds (e.g. chainsaw). Many features may be extracted and then they are compared with a known database which can be used to either classify or identify the sound.

In another embodiment, the received sound is buffered (e.g. 10 ms) and then a transformation is applied, such as, for example, FFT, MFCC etc. This representation is fed through a pretrained model which classifies it into a particular sound (e.g. a chainsaw). In another embodiment, both steps 120 and 130 are included the pretrained model (stored in a database local to the PPE device) where the representation is fed into the model and the enhanced sound is the output of the model.

In another embodiment, a model that is trained to separate different components on a logical basis rather than on frequency base (e.g. separating sound into chainsaw, jackhammer, . . . and residual).

In block 130, a model is applied to the parsed sound. The model may include amplifying the sound, as indicated in block 112, reducing the sound, as indicated in block 114, cancel the sound, as indicated in block 116, or adding an overlay to the sound, as indicated in block 118, such as an alert, an informational broadcast, or another sound. Other actions may also be taken, in conjunction with or instead of amplifying, reducing or canceling the sound, as indicated in block 126.

In block 140, the modified sound is broadcast through a speaker to a wearer of the PPE device. Only the modified sound may be transmitted, in one embodiment, as indicated in block 142. The modified sound may be recombined with other portions of the parsed sound stream, as indicated in block 144. In some embodiments, the sound stream is parsed into a plurality of sound portions, each of which undergoes modification. In such embodiments, as indicated by FIG. 3, the method steps of blocks 110, 120 and 130 may be repeated for each detected sound portion of a sound stream. Other sound broadcast configurations are possible, as indicated in block 146.

For example, a user of a PPE device in a construction zone may be operating a circular saw while a nearby cement truck is backing up. A supervisor may be calling out orders, either verbally or over a communications unit. The circular saw sound portion may be significantly reduced, and the supervisor sound portion may be amplified. A warning sound may be overlayed over the sound of the cement truck as a warning to the user that there is a potential hazard nearby. The sound portions—the reduced circular saw noise, amplified supervisor speech and warning overlay are then recombined before being broadcast to a user through a speaker of the PPE. In one embodiment, the sound portions are analyzed and modified in sequence, as indicated in block 130. However, in other embodiments a plurality of sound portions are analyzed and modified in parallel. This may allow for the sound to be broadcast to a user with less delay, but does require greater processing power.

Figure 4A:
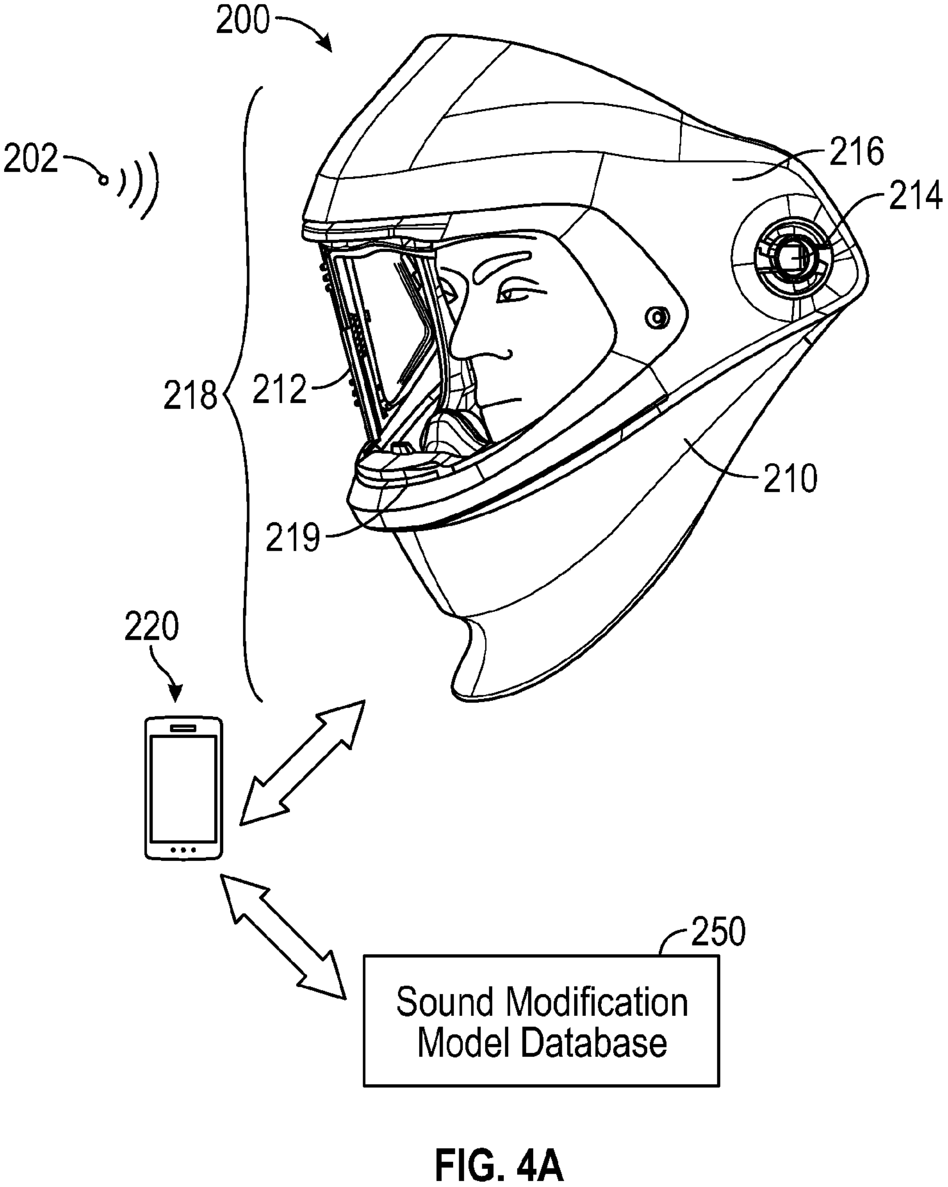
FIG. 4A illustrates a PPE sound modification system in an embodiment of the present invention.

FIG. 4A illustrates a PPE sound modification system in an embodiment of the present invention. System 200 may be useful with the hearing protection devices of FIG. 1, as well as other PPE devices. For example, Welding helmet 218, illustrated in FIG. 4, may be part of a sound modification system 200. Described in embodiments in this disclosure are sound modification systems that may be suitable for a variety of PPE systems, specifically any PPE system that includes a microphone that picks up ambient noise and a speaker that provides sound to a user. For example, a welding helmet 218 is illustrated in FIG. 4A and helmet 218 may include a built-in speaker, or may provide sound from a microphone to an in-ear speaker hearing protection unit, or an over-the-head hearing protection unit worn by a user under helmet 218.

FIG. 4A illustrates a welding helmet 218 in a system 200 comprising head-mounted device 210, visor attachment assembly 214 and one or more speakers (not shown) inside device 210 as well as one or more microphones (not shown) on an exterior or interior surface of device 210 or on the outside of the attenuating part of the hearing protection device to capture external sounds.

As illustrated, PPE device 200 is in communicative contact with a separate device 220, illustrated in FIG. 4 as a cellphone, which may have an application through which a user or wearer of PPE device 200 may interact with a sound modification model database 250. However, it is expressly contemplated that, in some embodiments, a user may communicate directly with database 250. For example, welding helmet 200 includes a screen 212 which may have augmented reality overlay abilities. A wearer may be able to, using audio, motion, or remote controller, interact with database 250 using a processer integrated into PPE 200 using screen 212. However, many PPE devices lack a screen and are designed to reduce processing power to preserve battery life. Therefore, in many embodiments, and as described herein, PPE devices are envisioned as interacting with database 250 using an intermediate device 220.

Additionally, while a cell phone 220 is illustrated in FIG. 4, it is expressly contemplated that other computing devices 220 are possible, including laptops, tablets, desktop computers, or other computing terminals able to interact, either in a wired or wireless capacity, with both of PPE device 200 and database 250.

Computing device 220 comprising one or more computer processors and a memory comprising instructions that may be executed by the one or more computer processors. Computing device 220 is communicatively coupled to the PPE device 200 and to a sound modification model database 250. Computing device 220 may include the same, a subset, or a superset of functionality and components illustrated and described in other figures of this disclosure. However, as described above, in some embodiments computing device 220 is integrated into either PPE device 200 or database 250, such that device 200 communicates directly with database 250.

Computing device 220 may be included in or attached to an article of personal protective equipment (e.g., system 200), may be positioned on or attached to the worker in a separate device external to head top 210, or may be in a remote computing device separate from the worker altogether (e.g., a remote server or safety terminal for users). Computing device 220 may communicate with the sound modification model database 250 in accordance with techniques of this disclosure.

In accordance with embodiments herein, microphones (not shown) associated with PPE 200 may receive a sound stream 202, parse out a specific sound portion, apply a model to the parsed sound portion, and broadcast the modified sound portion through, either alone or recombined as a modified sound stream 202, to a wearer of PPE 200 through a speaker (not shown).

In some embodiments, a processor responsible for recognizing sounds and applying appropriate sound models may detect a sound portion within sound stream 202 that is unfamiliar. The PPE processor may generate a query for database 250 regarding the unknown sound. The query may be sent via device 220, in one embodiment, either instantaneously, when device 200 is in a charging state, or when device 220 is connected to WIFI, for example. The query may be sent at other appropriate times, in other embodiments.

Sound modification model database 250 may automatically provide new sound models for download into a local storage of PPE 200, or may only provide sound models upon request or selection, using an application interface of device 220 or a screen associated with PPE 200, a safety station (e.g. station 15 illustrated in FIG. 2), a computer or laptop.

As described in greater detail herein, sound modification model database 250 includes functionality, in some embodiments, to classify or identify sounds currently 'unknown' to the PPE processor and provide a sound model that can be downloaded into a local memory of PPE device 200. Alternatively, in some embodiments, the sound recognition process is done using a processor of device 220. Other suitable configurations are also possible.

In some embodiments, at least some steps of method 100 are accomplished using a processor of device 220. In other embodiments, method 100 is accomplished solely using processors and memory integrated into device 200.

Described herein are systems and methods that are capable of providing alerts in response to certain recognized sounds. Said alerts can be provided using audio, visual or haptic feedback mechanisms within PPE 200 and/or using audio, visual or haptic feedback mechanisms of computing device 220. Additionally, in some embodiments either PPE device 200 or computing device 220 may store or send indications of generated alerts to another remote device or storage medium.

Computing device 220 may generate any type of indication of output. In some examples, the indication of output may be a message that includes various notification data. Notification data may include but is not limited to: an alert, warning, or information message: a type of personal protective equipment: a worker identifier: a timestamp of when the message was generated: a position of the personal protective equipment: one or more light intensities, or any other descriptive information. In some examples, the message may be sent to one or more computing devices as described in this disclosure and output for display at one or more user interfaces of output devices communicatively coupled to the respective computing devices. In some examples computing device 220 may receive an indication of where a sound source originated (e.g. based on a communication from a device generating a recognized sound) and generate the indicated output further based on the sound source and sound type was occurring.

Figure 4B:
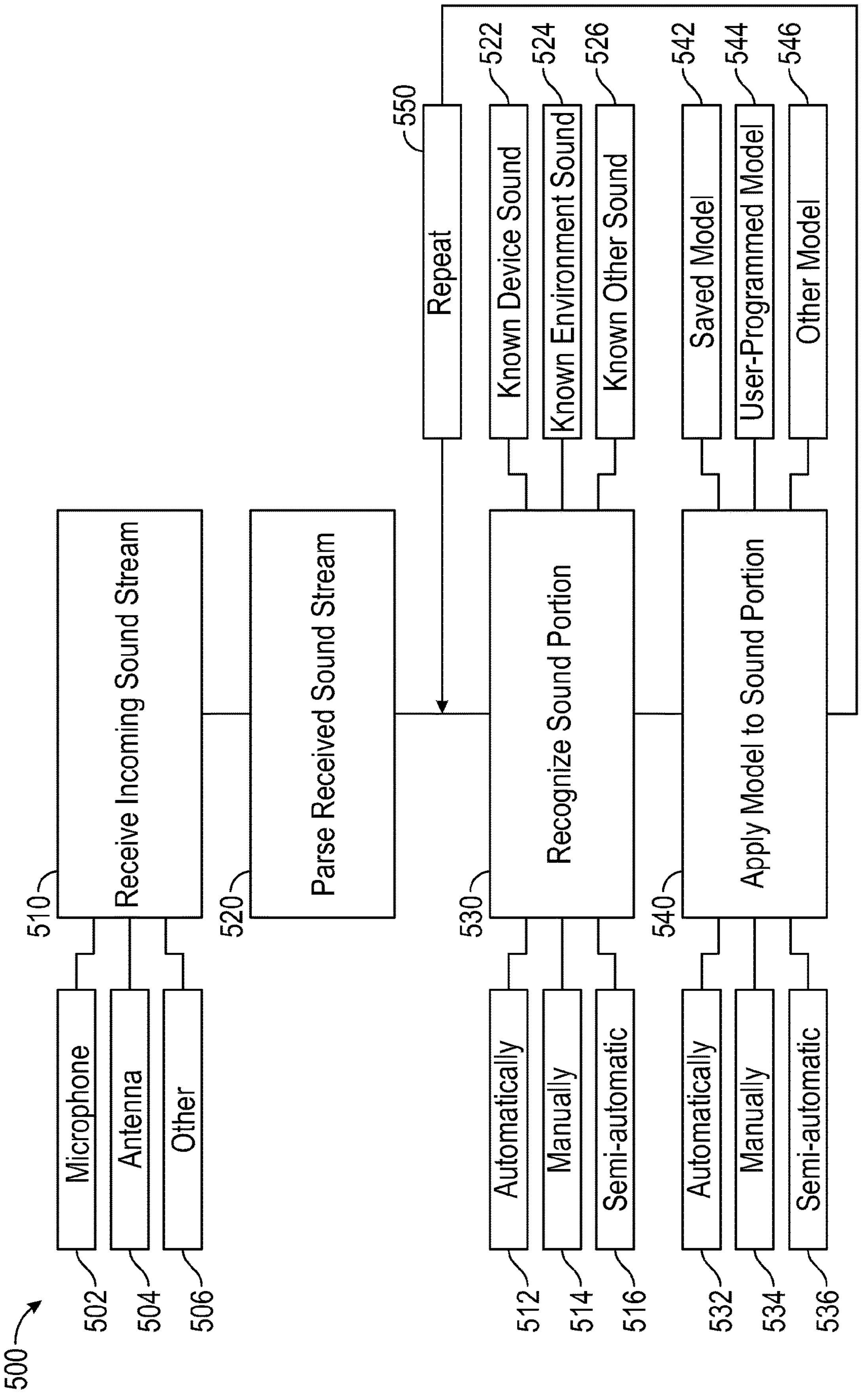
FIG. 4B illustrates a method of applying models to a sound stream in an embodiment of the present invention.

FIG. 4B illustrates a method of applying a model to a newly recognized sound in an embodiment of the present invention. Method 500 may be performed solely by a PPE device, in one embodiment. In other embodiments at least some functionality is performed by a separate computing device, such as a mobile device 220 in communication with a PPE device 200.

In block 510, an incoming sound stream is received by a PPE device. A microphone 502 may capture the sound, or it may be received by an antenna 504, or another mechanism 506 may provide the sound.

In block 520, the sound stream is parsed into a plurality of sound portions. For example, an individual wearing a PPE device standing outside may receive a sound stream that includes a wind sound portion, a rain sound portion, a speech portion, and a bird call portion.

Blocks 530 and 540 repeat, as indicated by block 550, for each of the plurality of sound portions. In turn, each sound portion is recognized, in block 530, and a model is applied, as indicated in block 540. The model may include doing nothing to the sound portion, amplifying the sound portion, reducing the sound portion, cancelling the sound portion, or adding an overlay to the sound portion.

In block 530, the sound portion is recognized. This may be done automatically 512, based on a manual trigger 514, or semi-automatically. For example, a PPE device, to save processing space, may only automatically parse sounds in certain frequency ranges or above certain decibel levels. A user may enjoy hearing the environmental sounds of wind, rain, birds and their companion, and, therefore, none of these sounds may necessitate adjustment.

The sound may be recognized as a known device sound 522, such as a gunshot in the distance, a known environmental sound 524, such as the wind or rain or bird sound, or a known other sound 526, such as the human speech sound portion.

In block 540, a model is applied to the sound portion based on the recognition. For example, a saved model 542, generated by a device manufacturer, may reduce the wind sound by 50%. The model may be a user-programmed model 544, for example an alert overlay that audibly names the bird associated with the bird call. The model 544 may also be a generated model in response to a user-request, for example a user uploading a bird sound and receiving a custom-programmed model 544 in response to the sound. The model may be generated by another source, such as another individual. The model may be applied automatically 532, for example each time the sound is recognized in block 530, or manually 534—for example only providing the audible bird name when a user requests. The model may be applied semi-automatically 536, in other embodiments.

Figure 5A:
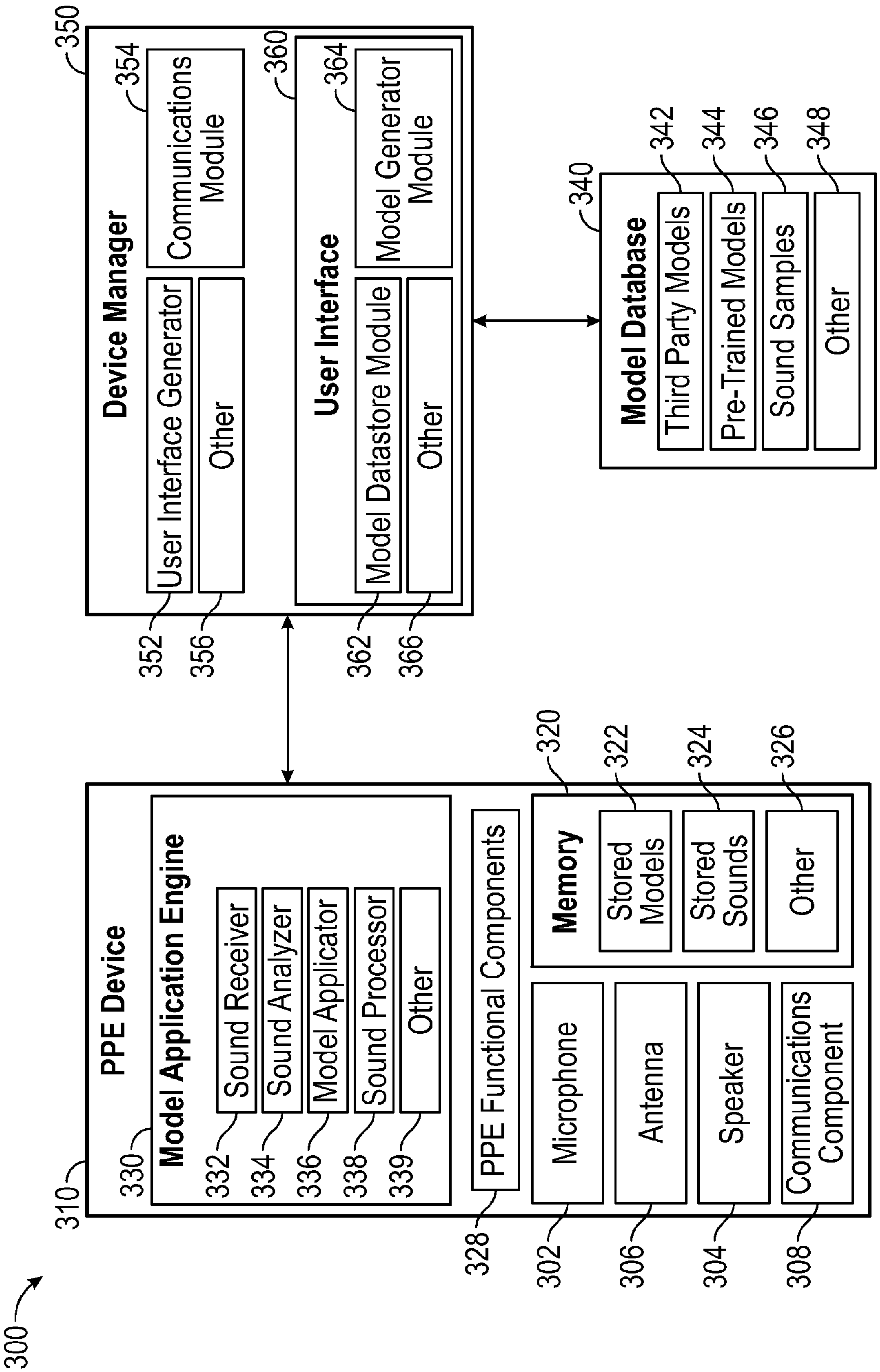
FIGS. 5A-5B illustrate schematics of a sound model management system in an embodiment of the present invention.
Figure 5B:
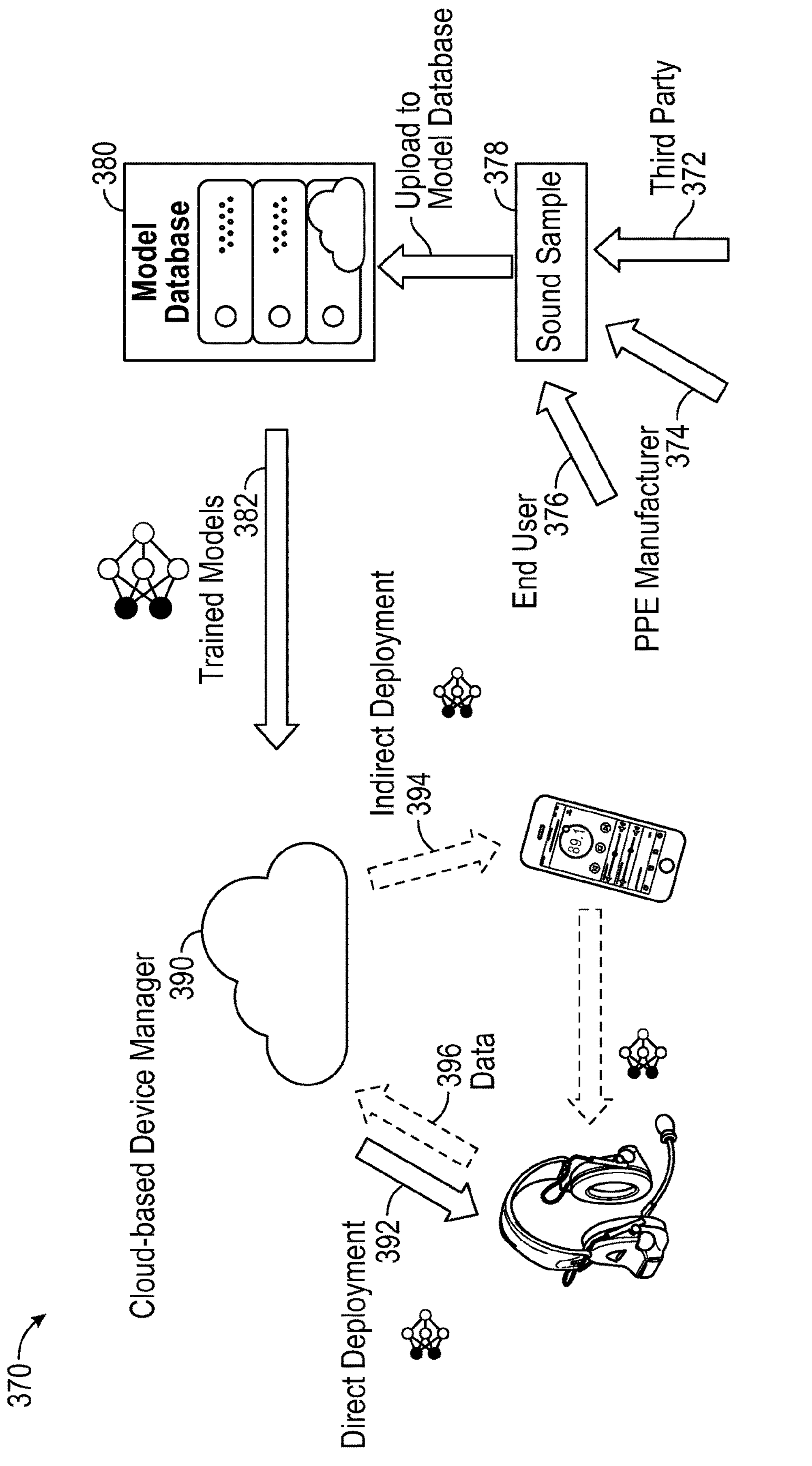

FIGS. 5A and 5B illustrate a schematic of a sound model management system in an embodiment of the present invention. System 300 represents interactions of a single PPE device 310 with model database 340. However, as contemplated in FIG. 2, it is expressly contemplated that systems and methods described herein may operate in a networked environment with other PPE devices 310 all accessing a single model database 340.

In the embodiment illustrated in FIG. 5, PPE device 310 accesses model database 340 via device manager 350. However, in other embodiments, it is expressly contemplated that PPE device 310 may interact with model database 340 directly such that at least some of the functionality of device manager 350 is incorporated into PPE device 310.

PPE device 310 includes one or more microphones 302 configured to pick up environmental sounds. PPE device 310 may also include one or more antenna 306 configured to receive signals from other devices, including other PPE devices 310, including audio signals that may be treated similarly to, or incorporated into a sound stream received by microphone 302. PPE device also includes one or more speakers 304 configured to broadcast sound to a wearer of PPE device 310. PPE device may also include a communications component 308 configured to communicate with device manager 350, or directly with model database 340.

PPE device 310 also includes a memory 320 which stores, among other data 326 necessary for the functional operation of PPE device 310, a database of stored sounds 324 and stored models 322.

PPE device also includes a model application engine 330 that analyzes ambient sounds and applies models as needed to improve an experience for a wearer of PPE device 310.

Sound receiver 332 receives a sound stream from a microphone 302 and parses the sound stream into individual sound portions. For example, a sound stream received in a construction zone may include the sound of a circular saw used near the wearer of PPE device 310, a nail gun used further away from the wearer of PPE device 310, an ambulance passing in the distance, and speech between two coworkers nearby. Sound receiver 332 may parse the sound stream into a circular saw portion, a nail gun portion, an ambulance portion, and a speech portion.

Sound analyzer 334 receives each sound portion from sound receiver 332 and checks stored sounds 324 to match a sound portion to a known sound. Stored sounds 324 may have been previously downloaded from model database 340, or may have been installed on PPE device 310 by a manufacturer. Sound analyzer 334 recognizes the circular saw sound portion, the ambulance sound portion, the speech portion, and the nail gun portion.

In some embodiments, sound analyzer separates a received sound into sound portions, similar to a Multi-Track audio stream. In another embodiment, a single model encompasses the sound receiver 332 and the sound analyzer 334, such that one model that does everything in one step, which may be faster for computing on an embedded device as it directly takes input stream and converts it to output stream. Therefore, in one step the incoming sound stream is divided into sound portions in almost real time by applying ML models. During the splitting process the sound portions are already identified with what correlates best with the models accessible to the sound analyzer 334.

Model applicator 336, based on an identification of a received sound portion, retrieves a stored model 322 and applies it to the recognized sound. For example, the ambulance sound may be cancelled, the nail gun sound may be reduced by 50%, the circular saw sound may be reduced by 90%, and the speech sound may be amplified 300%. The model applicator 336 may apply a model based on a degree of confidence in the sound identification. For example, the degree of confidence may vary between a minimum of 85-95% confidence.

Sound processor 338 recombines the sound portions into a format that can be broadcast through speaker 304. The modified sound stream, consisting of a 50% reduced nail gun sound portion, 90% reduced circular saw sound portion, and 300% amplified speech sound portion are provided to the user through speaker 304.

Model application engine 330 may also have other functionality. For example, model application engine, in some embodiments, sends a query to model database when a sound portion is unrecognized as one of stored sound classes 324.

PPE device 310 can be one of any suitable PPE devices that receive and provide sound to a user. PPE device may be a hearing protection device such as over-ear or in-ear hearing protection units. PPE device may also be a PAPR respirator, a welding helmet, or any other suitable PPE embodiment. PPE device 310 include any functional components 328 that are necessary for said personal protection function.

Model database 340 stores models and sound recordings that can be accessed using a suitable interface. In some embodiments, PPE device 310, using model application engine 330, may directly interface with model database 340 to retrieve new models as needed, and/or to provide an unrecognized sound for analysis. Model database 340 may include models from a variety of places. For example, a manufacture of PPE device 310 may provide pretrained models 344 based on expected interactions. For example, a manufacture of military hearing protection device may generate a variety of models based on gunshots, artillery sounds, explosions, etc., while a manufacture of a welding helmet may generate a variety of models based on different welding torches. Additionally, third parties may upload third-party models 342. For example, an individual owner of a PPE device may upload the sound of a saws-all cutting through PVC pipe, and may generate a model that reduces the sound of a saws-all cutting through PVC pipe by 70%. Additionally, a manufacturer of power tools may upload a variety of models of the different power tools acting on different materials.

Model database 340 also includes sound samples 346 that may be used to identify an unknown sound provided by PPE device 310. Sound samples 346 may be uploaded by PPE device 310, either directly or through device manager 350. Sound samples 346 may be uploaded automatically, for example as soon as they are recorded, or as soon as a triggering event occurs, such as PPE device 310 or device manager 350 connecting to a wireless network. Sounds may also be uploaded based on a user action, for example a user recording (using a recording function of a mobile device, using the microphone of said mobile device or remotely using the microphone(s) 302 of the PPE device 310, for example) a sound they wish to generate a model for.

Model database 340 may also include other data or functionality 348 in accordance with methods and systems described herein.

Device manager 350 is illustrated in FIG. 5 as separate from PPE device 310 and model database 340. In some embodiments, device manager 350 communicates with PPE device 310 using a wireless network such as WIFI, cellular network, Bluetooth®, NFC, or other suitable communication protocol. However, in other embodiments, device manager 350 requires a wired connection. Device manager 350 may communicate with model database 350, for example, using wireless, cellular, or cloud-based communication networks. Device manager communicates with PPE device 310 and model database 340 using one or more communications module 354. Device manager 350 may also include other suitable functionality 356.

Device manager 350 may be any suitable computing device such as a cellular phone, tablet, laptop computer, desktop computer, or other device. Device manager 350 has a screen configured to display a user interface 360, generated by user interface generator 352 based on a user actuating a model management application. The user interface 360 may provide a user a way to view models available for download to a PPE device 310 through model datastore module 362, which may also indicate models 322 stored on device 310 already. A user may add or remove models to stored model database 322 using model datastore module. Additionally, user interface 360 may present model generator module 364, which may allow for a user to generate a new model 342, for example based on a recorded sound. The recorded sound may be uploaded directly from PPE device 310, device manager 350, or from PPE device 310 via device manager 350. Additional sound recordings may also be uploadable, for example recordings of known or unknown sounds captured on a device other than PPE device 310. User interface 360 may also include other features or icons.

FIG. 5B illustrates another embodiment of a sound model management system. System 370 may receive sound samples from a variety of sources including, but not limited to a PPE device manufacturer 374, a third party 372, or an end-user 376, either an individual or an enterprise using PPE devices. A source 372, 374, 376 may provide a sound sample 378 to a model database 380, for example through a wired or wireless network connection.

Model database 380 may store both recognized and unrecognized sounds. Recognized sounds may already be associated with a model and provided to a cloud-based device manager 390 for deployment, either directly 392 or indirectly 394 to a PPE device. For unrecognized sounds, a trained model 382 may be generated by any of users 372, 374, 376, and may then be provided to cloud-based device manager 390. As illustrated in FIG. 5B, a PPE device may provide data 396, for example telemetry data, location data, ambient sound samples or user data, back to cloud-based device manager 390. In some embodiments a review process to ensure quality, safety and reliability of the models might be performed prior to providing the new trained models to the device manger 390.

Cloud-based device manager 390 may also have other functionality, for example communicating information to a plurality of PPE devices, in embodiments such as FIG. 2 where a PPE device is one of many within a network. In other embodiments, where a lone user of a PPE device interacts with model database 380, cloud-based device manager 390 may be accessed indirectly 394 using an application on a computing device.

Figure 6:
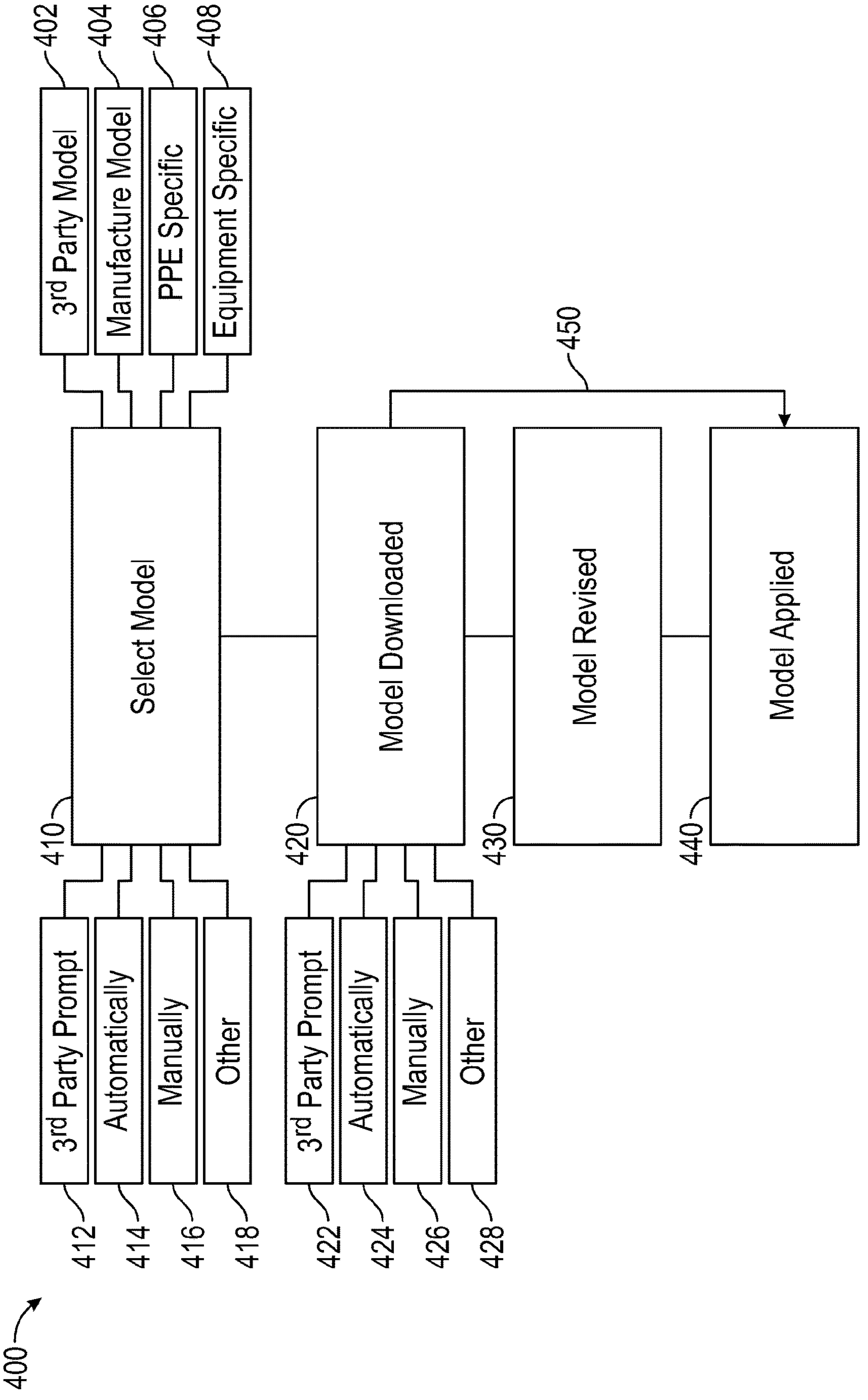
FIG. 6 illustrates a method of obtaining a new sound model for a PPE device in an embodiment of the present invention.

FIG. 6 illustrates a method of obtaining a new sound model for a PPE device in an embodiment of the present invention. Method 400 may be used to apply a newly obtained model to a sound portion of a sound stream. Method 400 may be practiced by a user interacting with a model download application, for example on a mobile phone or directly on a screen of a PPE device.

In block 410, using a user interface, a user selects a model. The model may be provided from a PPE device manufacture 404, a 3rd party 402 or another suitable source. The model may be specific to a PPE device, for example a model to reduce the sound of a PAPR respirator, or may be equipment-specific, such as a model to overlay an alert when heavy machinery is moving nearby.

The model may be selected automatically 414—for example, in response to a user's previously submitted sound sample. A device management system may push the model to the PPE device for download. Alternatively, the model may be selected manually 416. For example, an owner of an over-ear hearing protection device may have purchased a new circular saw and may search for, and download, a model corresponding to the sound that the circular saw makes when cutting through material. Models may be downloaded individually, for example a reduction by 50% in the noise the circular saw makes cutting through PVC, or as a bundle, for example reducing all known sounds the circular saw can make when cutting through materials by 50%. Additionally, a 3rd-party prompt 318 may indicate that the user should download a model. For example, an equipment manufacturer may provide a QR-code that, when scanned by a user's phone, selects models relevant to the equipment. Other methods of selecting a model are also expressly contemplated.

In block 420, a model is downloaded to the PPE device. In one embodiment, the model is downloaded directly to the PPE device from a model database. In another embodiment, the model is downloaded to the PPE device through a hub, such as a mobile phone. The model may be downloaded based on a prompt from a 3rd-party 422, automatically based on availability, for example, as indicated in block 424, manually, as indicated in block 426, or based on another suitable trigger 428.

As indicated by arrow 450, in some embodiments, a model is ready to be applied to a received sound portion by a PPE device, as indicated in block 440 to incoming sound when downloaded. However, as indicated in block 430, in some embodiments the model is revised prior to its use. For example, a computational device, such as a mobile phone, laptop, tablet or desktop computer, may allow a PPE device user to revise a model prior to its application. For example, downloading a model 420 may refer to the step of downloading a model from a cloud-based model database to an intermediate hub device, such as mobile device 220, which then can provide the model, in a second step, to PPE device 200.

In block 430, a selected model is revised, either while stored in the cloud-based model database, while stored on an intermediate hub device, or after downloaded to a memory of a PPE device. For example, an end user comfortable with the use of a circular saw may want the sound dampened more than someone new to its use. The end user may change the default dampening from 50% to 90%, for example.

Figure 7:
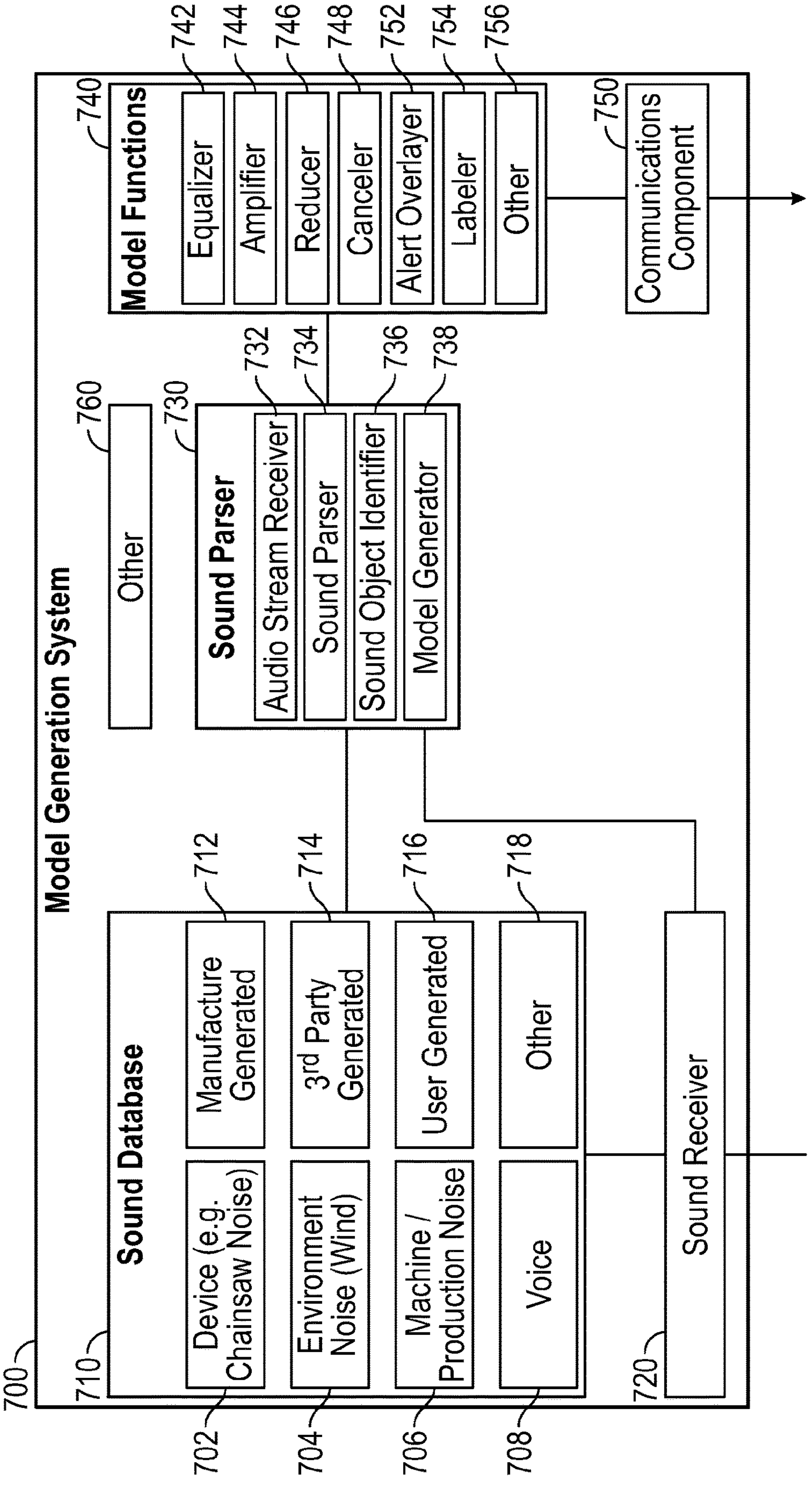
FIG. 7 illustrates a model data store in accordance with an embodiment of the present invention.

FIG. 7 illustrates a data generation system in accordance with an embodiment of the present invention. Model generation system 700 illustrates some of the data and functionality that may be ascribed to the model data stores described with respect to FIGS. 1-6. However, while model generation system 700 is illustrated as a separate, free-standing system, it is expressly contemplated that, in some embodiments, model generation system 700 is part of a cloud-based model database. For example, data store 700 may be managed by a device manufacturer, or may be managed locally by an enterprise user. Therefore, while model data store 700 illustrates a representation of some data and functionality that may be available in some embodiments, other embodiments may have different data or functionality than that illustrated.

Sound receiver 720 receives a sound stream from an external source, such as directly from a PPE device, from a computing device operating as a hub, or from another source, such as a recording device of a PPE user.

The received sound stream is provided to sound parsing module 730. In the event that the received sound stream contains multiple sounds, audio stream receiver 732 provides it to sound parser 734, which parses the sound into several sound portions, or sound objects, each of which is identified by sound object identifier 736. A model generator 738 generates a model based on one or more model functions 740.

Sound database 710 stores a plurality of known sound objects, including device sounds 702, such as a chainsaw cutting through wood, environmental noise 704, such as wind, a machine noise, such as the sound of a bulldozer, voice sounds 708, or other noises 718. Sound objects within sound database 710 may be generated by the PPE device manufacturer 712, by a 3rd party 714, or by an end user 716.

An end user, 3rd party or device manufacturer may generate a model by assigning a model function 740 and value to a sound object. For example, a sound object may be amplified (the sound function) by 50% (the value). Possible sound functions 740 include an equalizer 742, an amplifier 744, a reducer 746, a canceler 748, an alert overlayer 752 (e.g. a loud beep or other indication that danger is near), a labeler 754 (e.g. an audible label of the sound, such as the name of the bird generating the bird call, for example), or another suitable function 756.

Once a model is generated, communications component 750 provides it to a receiving device. The receiving device may be the source of the sound received by sound receiver 720, or the generated model may be provided to a model datastore for availability to other users. Model generation system 700 may include other functionality 760 as well as the functionality described with respect to FIG. 7.

Described herein are systems and methods of customizing an audio experience for a user. Many different functionalities are described, in FIGS. 1-7, with respect to a given device. However, while functionality is illustrated in several figures with respect to a given device, it is expressly contemplated that, in some embodiments, an illustrated functionality is performed by a different device.

However, in order to minimize delay, it may be preferred, in at least some embodiments, for at least some of the methods and systems described herein to be wholly contained within the PPE device, such that time is not lost transferring parsed sound objects back and forth between the PPE device and either a computing device or a model database.

Similarly, while models are discussed herein as being generated or revised, it may be preferred that the generation or revision take place on a device other than the PPE device, as the software size requirements could be prohibitive for a PPE device.

Figure 8:
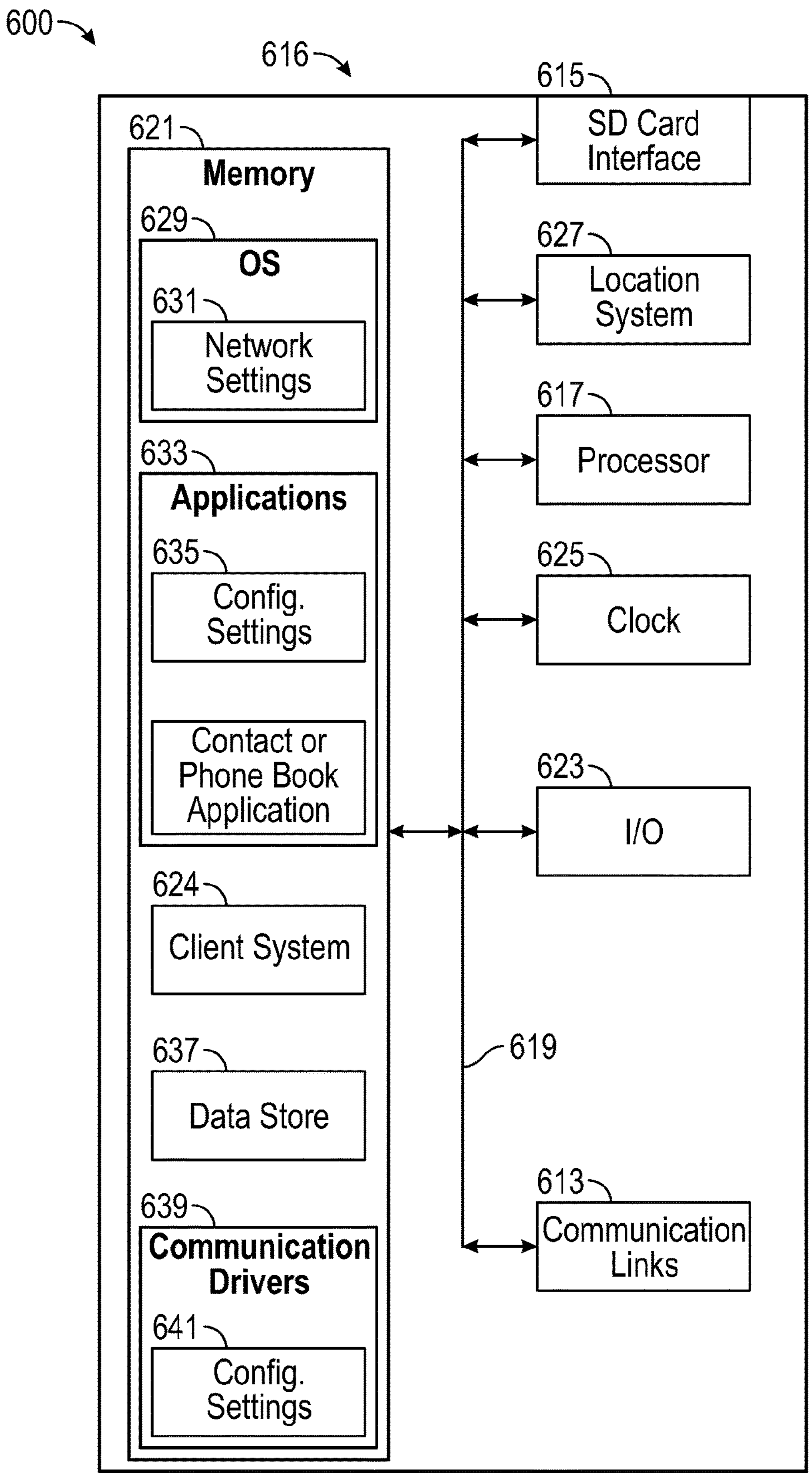
FIGS. 8-10 illustrate example devices that can be used in embodiments herein.
Figure 9:
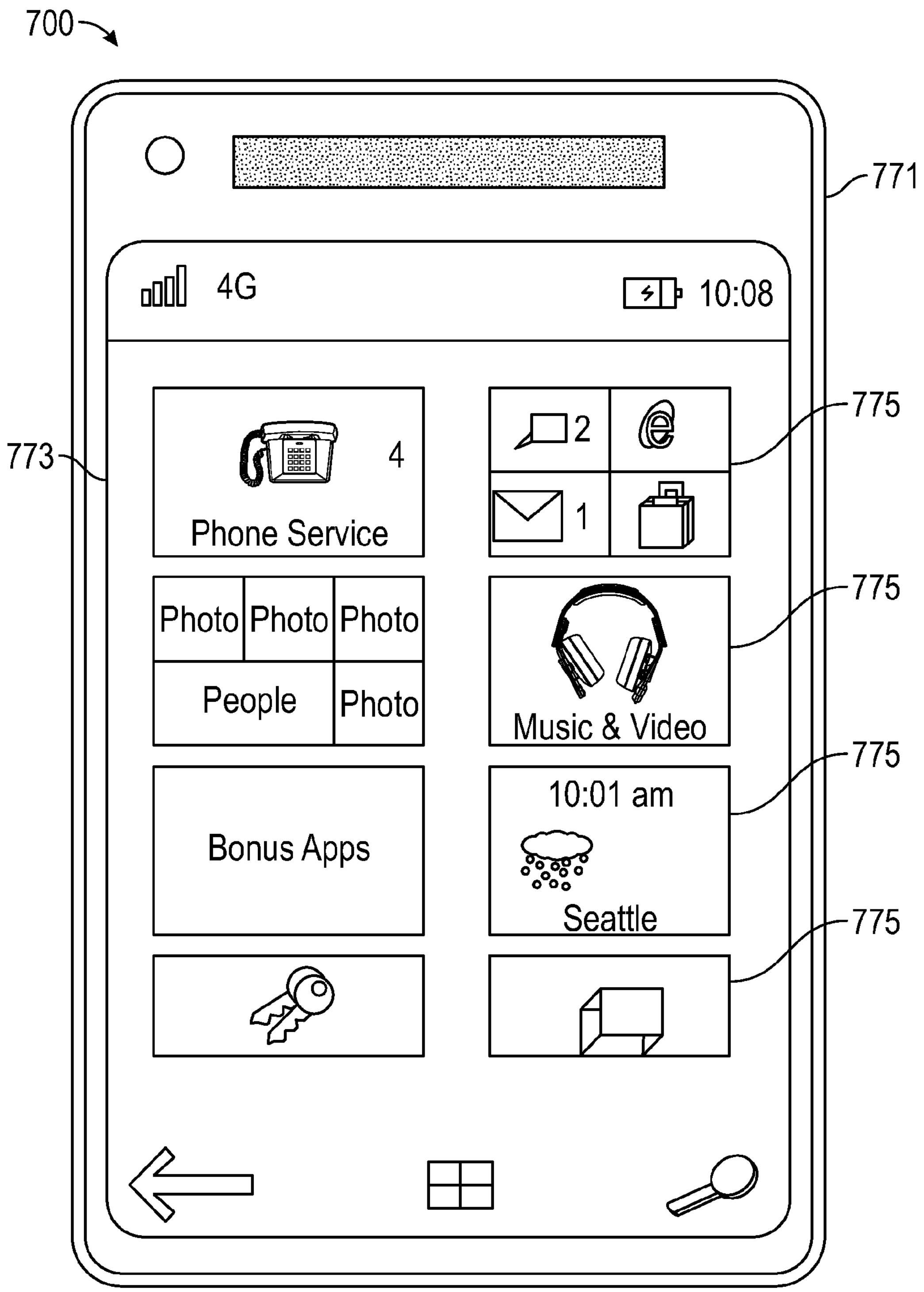
Figure 10:
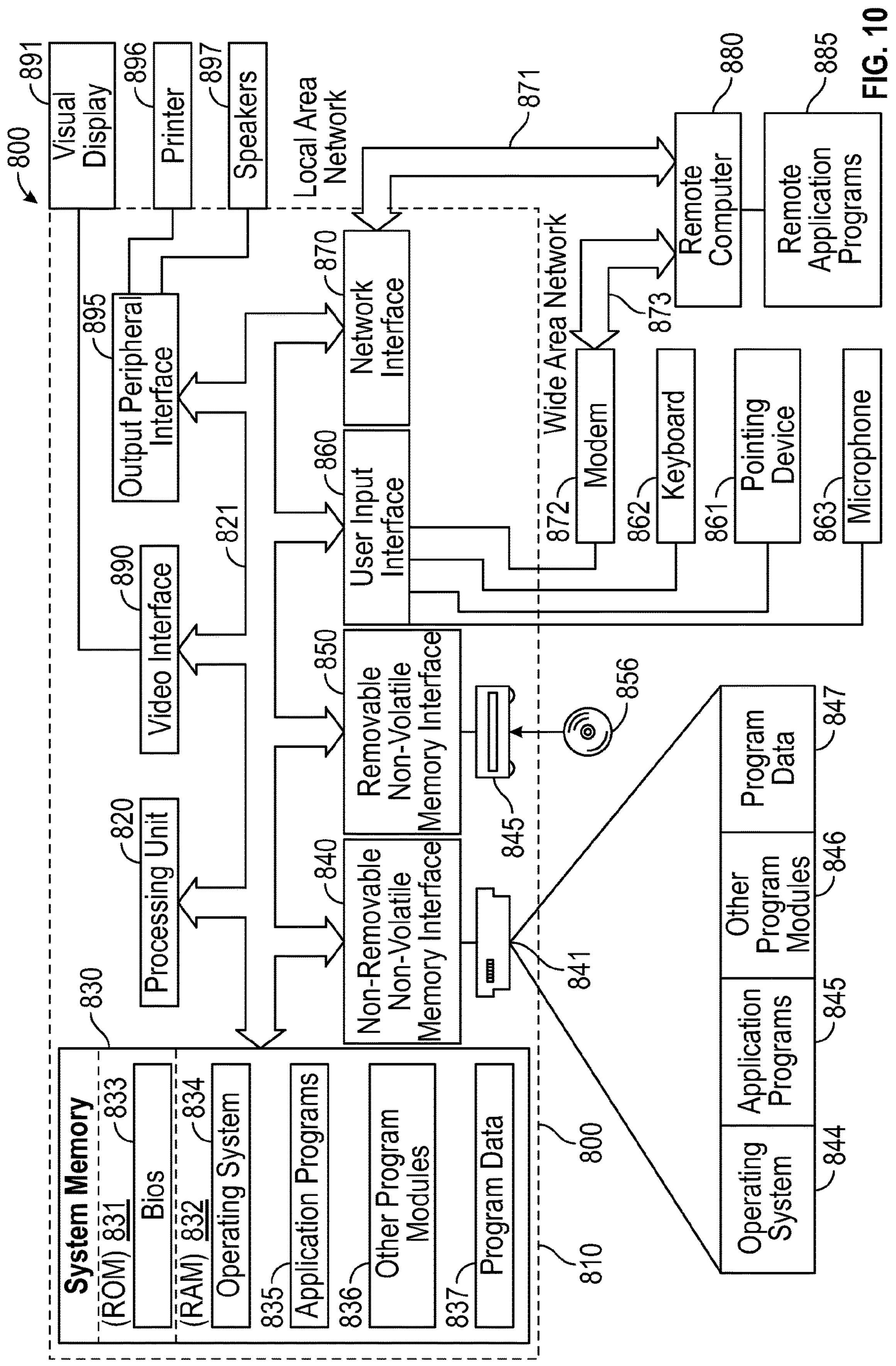

FIGS. 8-10 illustrate example devices that can be used in the embodiments shown in previous Figures. FIG. 8 illustrates an example mobile device that can be used in the embodiments shown in previous Figures. FIG. 8 is a simplified block diagram of one illustrative example of a handheld or mobile computing device that can be used as either a worker's device or a supervisor/safety officer device, for example, in which the present system (or parts of it) can be deployed. For instance, a mobile device can be deployed in the operator compartment of computing device for use in generating, processing, or displaying the data.

FIG. 8 provides a general block diagram of the components of a mobile cellular device 616 that can run some components shown and described herein. Mobile cellular device 616 interacts with them or runs some and interacts with some. In the device 616, a communications link 613 is provided that allows the handheld device to communicate with other computing devices and under some embodiments provides a channel for receiving information automatically, such as by scanning. Examples of communications link 613 include allowing communication though one or more communication protocols, such as wireless services used to provide cellular access to a network, as well as protocols that provide local wireless connections to networks.

In other examples, applications can be received on a removable Secure Digital (SD) card that is connected to an interface 615. Interface 615 and communication links 613 communicate with a processor 617 (which can also embody a processor) along a bus 619 that is also connected to memory 621 and input/output (I/O) components 623, as well as clock 625 and location system 627.

I/O components 623, in one embodiment, are provided to facilitate input and output operations and the device 616 can include input components such as buttons, touch sensors, optical sensors, microphones, touch screens, proximity sensors, accelerometers, orientation sensors and output components such as a display device, a speaker, and or a printer port. Other I/O components 623 can be used as well.

Clock 625 illustratively comprises a real time clock component that outputs a time and date. It can also provide timing functions for processor 617.

Illustratively, location system 627 includes a component that outputs a current geographical location of device 616. This can include, for instance, a global positioning system (GPS) receiver, a LORAN system, a dead reckoning system, a cellular triangulation system, or other positioning system. It can also include, for example, mapping software or navigation software that generates desired maps, navigation routes and other geographic functions.

Memory 621 stores operating system 629, network settings 631, applications 633, application configuration settings 635, data store 637, communication drivers 639, and communication configuration settings 641. Memory 621 can include all types of tangible volatile and non-volatile computer-readable memory devices. It can also include computer storage media (described below). Memory 621 stores computer readable instructions that, when executed by processor 617, cause the processor to perform computer-implemented steps or functions according to the instructions. Processor 617 can be activated by other components to facilitate their functionality as well. It is expressly contemplated that, while a physical memory store 621 is illustrated as part of a device, that cloud computing options, where some data and/or processing is done using a remote service, are available.

FIG. 9 shows that the device can also be a smart phone 771. Smart phone 771 has a touch sensitive display 773 that displays icons or tiles or other user input mechanisms 775. Mechanisms 775 can be used by a user to run applications, make calls, perform data transfer operations, etc. In general, smart phone 771 is built on a mobile operating system and offers more advanced computing capability and connectivity than a feature phone. Note that other forms of the devices are possible.

FIG. 10 is one example of a computing environment in which elements of systems and methods described herein, or parts of them (for example), can be deployed. With reference to FIG. 10, an example system for implementing some embodiments includes a general-purpose computing device in the form of a computer 810. Components of computer 810 may include, but are not limited to, a processing unit 820 (which can comprise a processor), a system memory 830, and a system bus 821 that couples various system components including the system memory to the processing unit 820. The system bus 821 may be any of several types of bus structures including a memory bus or memory controller, a peripheral bus, and a local bus using any of a variety of bus architectures. Memory and programs described with respect to systems and methods described herein can be deployed in corresponding portions of FIG. 10.

Computer 810 typically includes a variety of computer readable media. Computer readable media can be any available media that can be accessed by computer 810 and includes both volatile/nonvolatile media and removable/non-removable media. By way of example, and not limitation, computer readable media may comprise computer storage media and communication media. Computer storage media is different from, and does not include, a modulated data signal or carrier wave. It includes hardware storage media including both volatile/nonvolatile and removable/non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 810. Communication media may embody computer readable instructions, data structures, program modules or other data in a transport mechanism and includes any information delivery media. The term "modulated data signal" means a signal that has one or more of its characteristics set or changed in such a manner as to encode information in the signal.

The system memory 830 includes computer storage media in the form of volatile and/or nonvolatile memory such as read only memory (ROM) 831 and random-access memory (RAM) 832. A basic input/output system 833 (BIOS) containing the basic routines that help to transfer information between elements within computer 810, such as during start-up, is typically stored in ROM 831. RAM 832 typically contains data and/or program modules that are immediately accessible to and/or presently being operated on by processing unit 820. By way of example, and not limitation, FIG. 10 illustrates operating system 834, application programs 835, other program modules 836, and program data 837.

The computer 810 may also include other removable/non-removable and volatile/nonvolatile computer storage media. By way of example only, FIG. 10 illustrates a hard disk drive 841 that reads from or writes to non-removable, nonvolatile magnetic media, nonvolatile magnetic disk 852, an optical disk drive 855, and nonvolatile optical disk 856. The hard disk drive 841 is typically connected to the system bus 821 through a non-removable memory interface such as interface 840, and optical disk drive 855 are typically connected to the system bus 821 by a removable memory interface, such as interface 850.

Alternatively, or in addition, the functionality described herein can be performed, at least in part, by one or more hardware logic components. For example, and without limitation, illustrative types of hardware logic components that can be used include Field-programmable Gate Arrays (FPGAs), Application-specific Integrated Circuits (e.g., ASICS), Application-specific Standard Products (e.g., ASSPs), System-on-a-chip systems (SOCs), Complex Programmable Logic Devices (CPLDs), etc.

The drives and their associated computer storage media discussed above and illustrated in FIG. 10, provide storage of computer readable instructions, data structures, program modules and other data for the computer 810. In FIG. 13, for example, hard disk drive 841 is illustrated as storing operating system 844, application programs 845, other program modules 846, and program data 847. Note that these components can either be the same as or different from operating system 834, application programs 835, other program modules 836, and program data 837.

A user may enter commands and information into the computer 810 through input devices such as a keyboard 862, a microphone 863, and a pointing device 861, such as a mouse, trackball or touch pad. Other input devices (not shown) may include a joystick, game pad, satellite receiver, scanner, a gesture recognition device, or the like. These and other input devices are often connected to the processing unit 820 through a user input interface 860 that is coupled to the system bus but may be connected by other interface and bus structures. A visual display 891 or other type of display device is also connected to the system bus 821 via an interface, such as a video interface 890. In addition to the monitor, computers may also include other peripheral output devices such as speakers 897 and printer 896, which may be connected through an output peripheral interface 895.

The computer 810 is operated in a networked environment using logical connections, such as a Local Area Network (LAN) or Wide Area Network (WAN) to one or more remote computers, such as a remote computer 880. The computer may also connect to the network through another wired connection. A wireless network, such as WiFi may also be used.

When used in a LAN networking environment, the computer 810 is connected to the LAN 871 through a network interface or adapter 870. When used in a WAN networking environment, the computer 810 typically includes a modem 872 or other means for establishing communications over the WAN 873, such as the Internet. In a networked environment, program modules may be stored in a remote memory storage device. FIG. 10 illustrates, for example, that remote application programs 885 can reside on remote computer 880.

In the present detailed description of the preferred embodiments, reference is made to the accompanying drawings, which illustrate specific embodiments in which the invention may be practiced. The illustrated embodiments are not intended to be exhaustive of all embodiments according to the invention. It is to be understood that other embodiments may be utilized and structural or logical changes may be made without departing from the scope of the present invention. The following detailed description, therefore, is not to be taken in a limiting sense, and the scope of the present invention is defined by the appended claims.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

If implemented in software, the techniques may be realized at least in part by a computer-readable medium comprising instructions that, when executed in a processor, performs one or more of the methods described above. The computer-readable medium may comprise a tangible computer-readable storage medium and may form part of a computer program product, which may include packaging materials. The computer-readable storage medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable storage medium may also comprise a non-volatile storage device, such as a hard-disk, magnetic tape, a compact disk (CD), digital versatile disk (DVD), Blu-ray disk, holographic data storage media, or other non-volatile storage device.

The term "processor," as used herein may refer to any of the foregoing structure or any other structure suitable for implementation of the techniques described herein. In addition, in some aspects, the functionality described herein may be provided within dedicated software modules or hardware modules configured for performing the techniques of this disclosure. Even if implemented in software, the techniques may use hardware such as a processor to execute the software, and a memory to store the software. In any such cases, the computers described herein may define a specific machine that is capable of executing the specific functions described herein. Also, the techniques could be fully implemented in one or more circuits or logic elements, which could also be considered a processor.

A personal protective equipment device is presented that includes a speaker configured to provide a modified sound to a user. The PPE device also includes a microphone configured to capture an ambient sound stream. The PPE device also includes a sound analyzer that receives the ambient sound stream from the microphone and identifies a first sound in the ambient sound. The PPE device also includes a sound processor that applies a model to the first sound, based on the sound identification, to obtain the modified first sound. The model changes a characteristic of the identified sound and the modified sound is provided to the speaker. The model comprises an algorithm stored locally in a model database within a memory of the personal protective equipment device.

The device may be implemented such that the model database is communicably coupled to a remote database comprising a plurality of downloadable models.

The device may be implemented such that one of the plurality of models comprises a downloaded model originating from a third party.

The device may be implemented such that the model comprises an amplifier, and the sound is amplified by the sound processor.

The device may be implemented such that the model comprises a canceler, and the sound is removed by the sound processor.

The device may be implemented such that the model comprises a reducer, and the sound is reduced by the sound processor.

The device may be implemented such that the model comprises an alert overlay, and an alert overlay is added to the identified sound or re-combined sound portions.

The device may be implemented such that the model is a first model and the sound analyzer identifies a second sound, and applies a second model to the second sound to obtain a modified second sound.

The device may be implemented such that the second model is different from the first model.

The device may be implemented such that the modified sound is a modified first sound, and the sound processor recombines the modified first sound and the modified second sound to obtain the modified sound.

The device may also include a communications component configured to receive a model from a second device.

The device may be implemented such that the communications component operates under a 2.4 GHz protocol or a 5 GHz protocol.

The device may be implemented such that the device is a hearing protection device, and the hearing protection device provides level dependent hearing protection.

The device may be implemented such that the hearing protection device is an in-ear hearing protection device.

The device may be implemented such that the hearing protection device is an over-ear headset.

The device may be implemented such that the hearing protection device is an in-ear hearing protection unit.

The device may be implemented such that the device is a powered air purifying respirator.

The device may be implemented such that the device is a welding helmet with a hearing protection unit.

The device may be implemented such that, if a sound portion is detected and unrecognized by the sound analyzer, it is provided, using the communications component, to the second device.

The device may be implemented such that the modified sound comprises a recombined first modified sound with a second modified sound.

The device may be implemented such that the modified sound comprises the ambient sound with the modified sound less the first sound.

The device may be implemented such that model database comprises a downloaded model.

An acoustic model management system is presented that includes a sound database comprising a plurality of sound objects. The system also includes a model database comprising a plurality of models, each of which is applicable to one or more of the sound objects. The system also includes a sound parsing system. The sound parsing system includes a sound receiver configured to receive a sound stream, a sound analyzer configured to parse a plurality of sound portions from the sound stream, a sound selector configured to select one of the plurality of sound portions for manipulation and a model generator configured to generate a model to apply to the selected sound portion. The generated model, and a sound object corresponding to the selected sound portion is stored in the model database. The system also includes a user interface generator configured to generate a user interface for a user to interact with the sound parsing system, select the sound portion, using the sound selector, and generate a model, using the model generator. The system also includes a download manager configured to provide the identified sound portion and the generated model to a personal protective equipment device memory such that a processor of the personal protection equipment device can automatically identify the sound portion in an incoming audio stream and apply the generated model automatically such that, when identified, the sound type is manipulated according to the model prior to being broadcast to a user.

The acoustic model management system may be implemented such that the user generates the model by selecting a model function to apply to the sound portion. The model function is an amplifying, reducing, equalizing or cancelling function.

The acoustic model management system may be implemented such that the model function also comprises applying an overlay to the sound portion. The overlay is an alert overlay or a label corresponding to the sound portion.

The acoustic model management system may be implemented such that the sound receiver receives the sound stream from a personal protective equipment device.

The acoustic model management system may be implemented such that the sound receiver receives the sound stream from a computing device.

A method of processing sound in a personal protective equipment device is presented. The method includes receiving an ambient sound stream. The method also includes parsing, using a model application engine, the ambient sound into a plurality of sound objects. The method also includes identifying one of the sound objects, using a sound analyzer. The method also includes retrieving a model from a model database based on the identified sound object. The method also includes processing the ambient sound by applying the retrieved model to the identified sound object to obtain a modified sound object and recombining the plurality of sound objects into a modified sound. The modified sound includes the modified sound object instead of the identified sound object. The method also includes broadcasting the modified sound to a wearer of the personal protection device through a speaker of the personal protection device.

The method may be implemented such that the ambient sound is received through a microphone positioned on an exterior of the personal protection device.

The method may be implemented such that the personal protective equipment device is an in-ear hearing protection device, an over-ear hearing protection device, a welding helmet or a powered air purifying respirator.

The method may also include identifying a second sound object, using the sound analyzer, retrieving a model from a model database based on the identified second sound object, processing the identified second sound object into a second modified sound object, and recombining the first and second modified sound object into the modified sound.

The method may also include identifying one of the plurality of sound objects as an unknown sound object and sending the unknown sound object to a second device for identification.

The method may also include applying a level dependent function to the unknown sound object and recombining it into the modified sound object.

The method may also include receiving a new model corresponding to the unknown sound object, applying the new model to the unknown sound object, and recombining it into the modified sound object.

The method may be implemented such that the steps of parsing, identifying, retrieving and processing is done automatically when the sound stream is received.

EXAMPLES

Example 1: Recognizing a Sound Portion

Figure 11A:
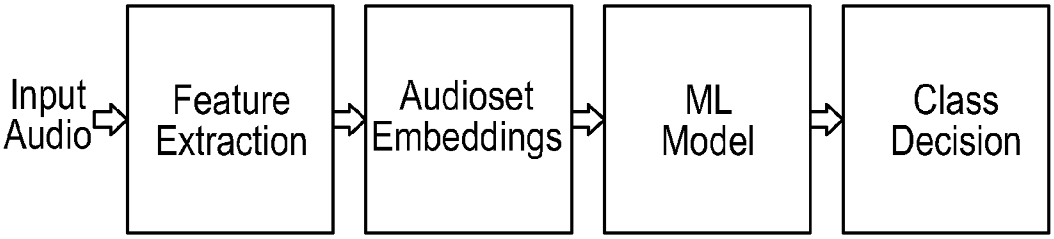
FIGS. 11A-11D illustrate an example extraction and validation of an identified sound object.

A machine learning (ML) model was trained on dataset to classify the audio into different classes. As illustrated in FIG. 11A, an audio input was subjected to feature extraction, audioset embeddings, applied machine learning modeling and a class decision.

To achieve this initially the audio features for the model were extracted using a VGG-inspired acoustic model described in Hershey et. al., *CNN Architectures for Large-Scale Audio Classification, International Conference on Acoustics, Speech and Signal Procesing* (*ICASSP*), *IEEE* (2017). The model was trained on a preliminary version of the You Tube-8M Segments Dataset. The features were PCA-ed and quantized to be compatible with the audio features provided with YouTube-8M.

A machine learning (ML) model was trained on Audioset dataset to classify the audio into different classes. AudioSet dataset is a large-scale collection of human-labeled 10-second sound clips drawn from YouTube videos. Feature embedding and extraction was done using a pretrained model provided by google. The ML model is using the output of the embeddings step and runs a classification (this can be standards classification models but may also include deep learning models such as multi-layer-perceptrons (MLP) or Long-Short-Term-Memory (LSTM) networks.

Figure 11B:
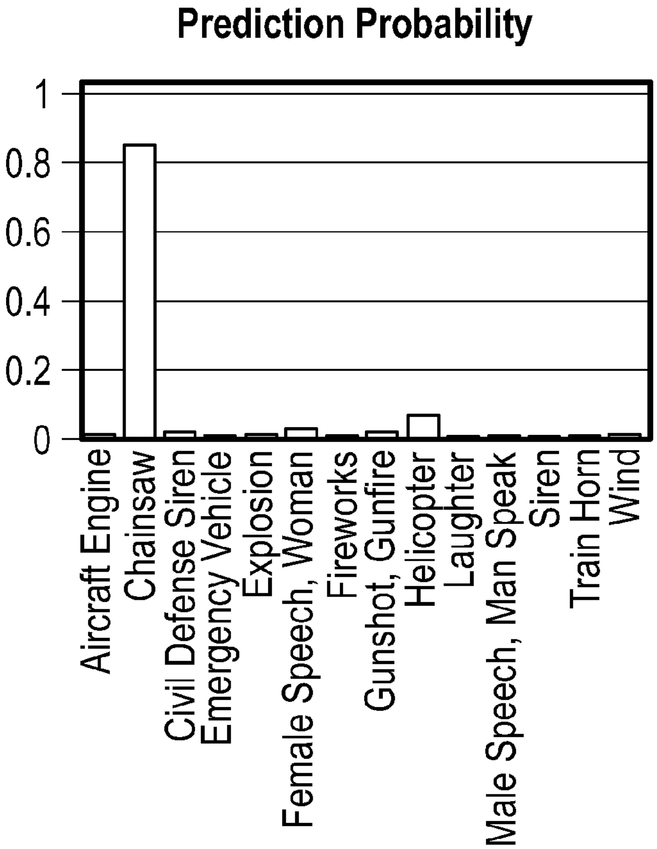
Figure 11C:
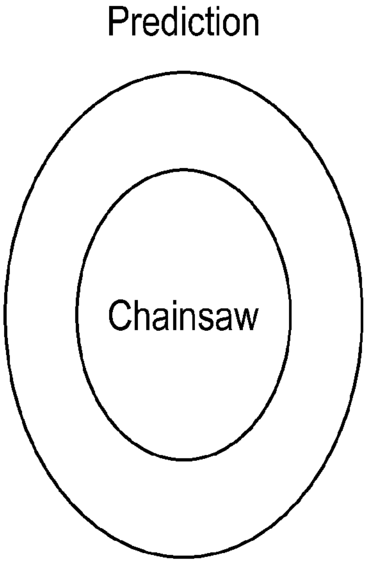

As illustrated in FIGS. 11B, a probability is generated for each of a plurality of possible sounds that might match the captured sound. FIG. 11C illustrates how, based on a database of sound objects, a parsed sound portion is identified as a Chainsaw.

Figure 11D:
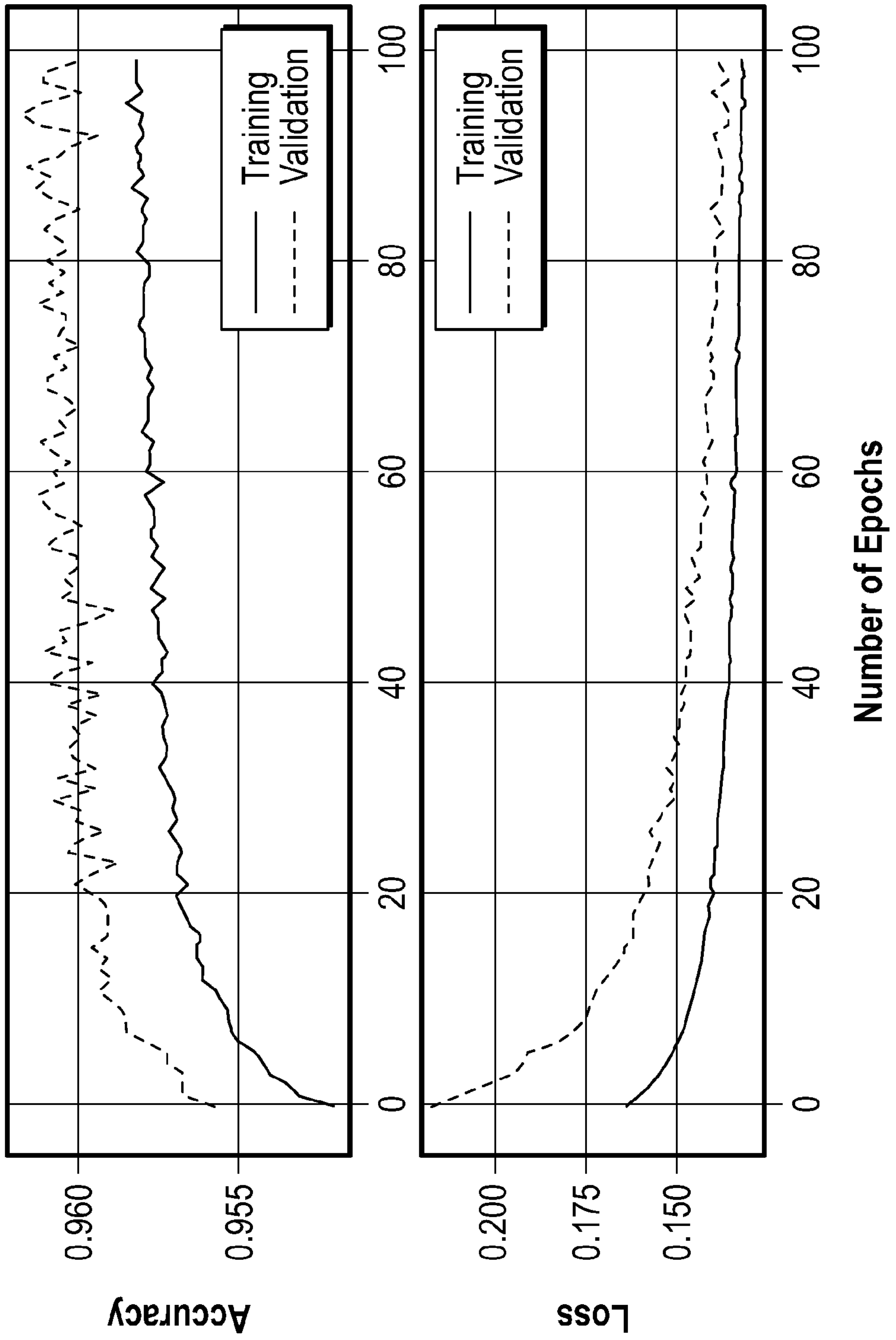

FIG. 11D illustrates accuracy and loss, which were used as a metrics to measure the model performance. Accuracy describes the accuracy of the Machine learning model to predict the correct class. Loss is an internal metric of the machine learning model to optimize for (loss→0). Within neural networks during training the data is presented several times to the model. Each cycle is one epoch.

Example 2: Sound Model Management User Interface

Figure 12:
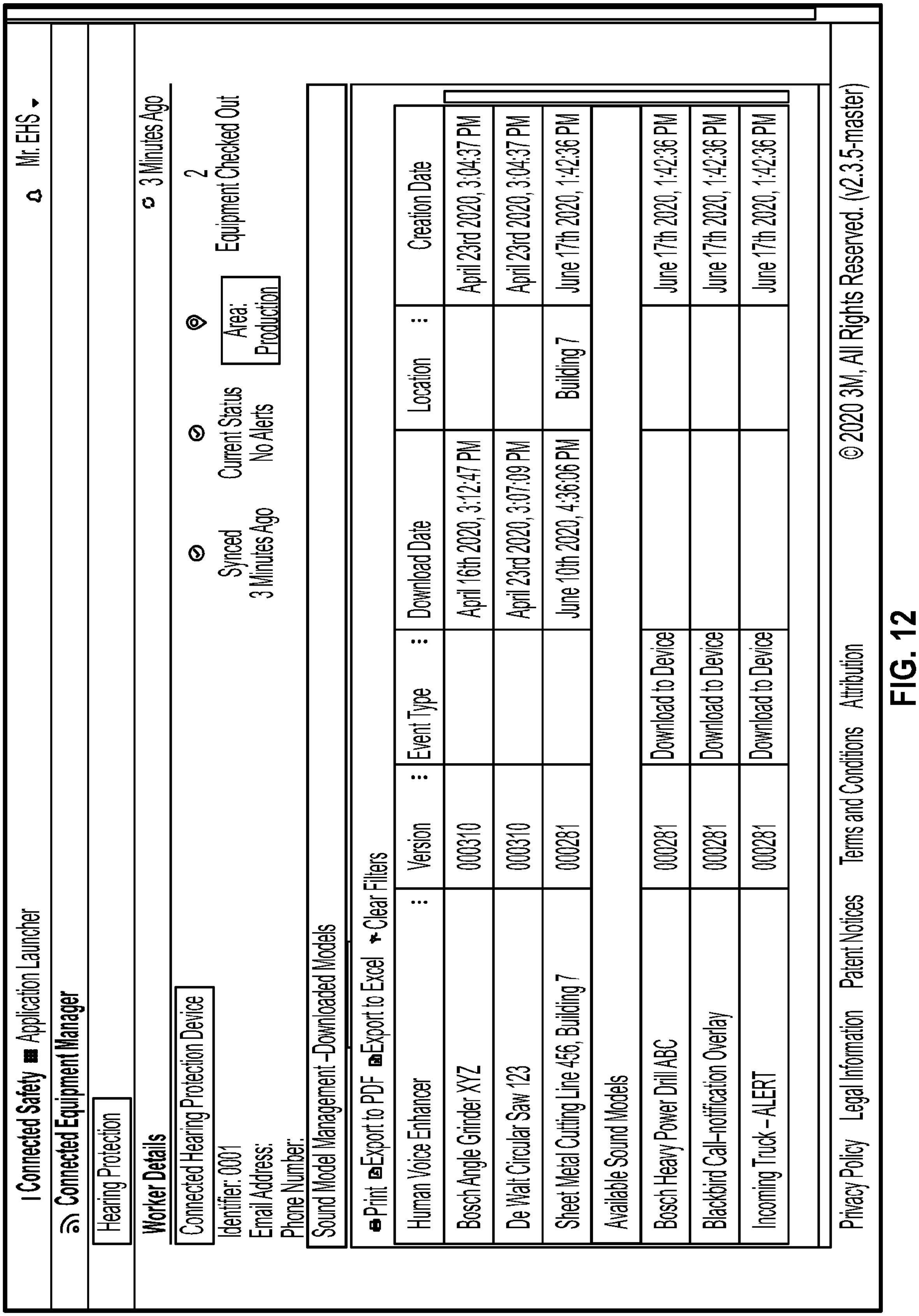
FIG. 12 illustrates an example user interface structure that may be used in embodiments herein.

FIG. 12 illustrates an example user interface for a sound model management system. A number of downloaded models may be illustrated. Each model may be updated, or updateable by a model originator, and may, therefore, have a version number and a creation date. A download or available date may be listed, as well as a status of whether a given model has been downloaded.

What is claimed is:

1. A personal protective equipment device comprising:

a speaker configured to provide a modified sound to a user;

a microphone configured to capture an ambient sound stream;

a sound analyzer that receives the ambient sound stream from the microphone and identifies a first sound in the ambient sound stream;

a sound processor that applies a model to the first sound, based on the sound identification, to obtain the modified first sound, wherein the model changes a characteristic of the first sound, and wherein the modified sound is provided to the speaker; and wherein the model comprises an algorithm stored locally in a model database within a memory of the personal protective equipment device.

2. The device of claim 1, wherein the model database is communicably coupled to a remote database comprising a plurality of downloadable models.

3. The device of claim 1, wherein the model comprises at least one of:

an amplifier, and wherein the sound is amplified by the sound processor;

a canceler, and wherein the sound is removed by the sound processor; or a reducer, and wherein the sound is reduced by the sound processor.

4. The device of claim 1, wherein the model comprises an alert overlayer, and wherein an alert overlay is added to the first sound or re-combined sound portions.

5. The device of claim 1, wherein the model is a first model and wherein the sound analyzer identifies a second sound, and applies a second model to the second sound to obtain a modified second sound.

6. The device of claim 5, wherein the modified sound is a modified first sound, and wherein the sound processor recombines the modified first sound and the modified second sound to obtain the modified sound.

7. The device of claim 5, and further comprising a communications component configured to receive a model from a second device.

8. The device of claim 7, and wherein, if a sound portion is detected and unrecognized by the sound analyzer, it is provided, using the communications component, to the second device.

9. The device of claim 1, wherein the device is a hearing protection device, and wherein the hearing protection device provides level dependent hearing protection.

10. The device of claim 1, wherein the modified sound comprises a recombined first modified sound with a second modified sound.

11. An acoustic model management system comprising:

a sound database comprising a plurality of sound objects;

a model database comprising a plurality of models, each of which is applicable to one or more of the sound objects;

a sound parsing system comprising:

a sound receiver configured to receive a sound stream;

a sound analyzer configured to parse a plurality of sound portions from the sound stream;

a sound selector configured to select one of the plurality of sound portions for manipulation; and a model generator configured to generate a model to apply to the selected sound portion, wherein the generated model, and a sound object corresponding to the selected sound portion is stored in the model database;

a user interface generator configured to generate a user interface for a user to interact with the sound parsing system, select the sound portion, using the sound selector, and generate a model, using the model generator; and a download manager configured to provide the selected sound portion and the generated model to a personal protective equipment device memory such that a processor of the personal protection equipment device can automatically identify the sound portion in an incoming audio stream and apply the generated model automatically such that, when identified, the sound portion is manipulated according to the model prior to being broadcast to a user.

12. The acoustic model management system of claim 11, wherein the user generates the model by selecting a model function to apply to the selected sound portion, wherein the model function is an amplifying, reducing, equalizing or cancelling function.

13. The acoustic model management system of claim 12, wherein the model function also comprises applying an overlay to the selected sound portion, wherein the overlay is an alert overlay or a label corresponding to the sound portion.

14. The acoustic model management system of claim 11, wherein the sound receiver receives the sound stream from a personal protective equipment device.

15. The acoustic model management system of claim 11, wherein the sound receiver receives the sound stream from a computing device.

16. A method of processing sound in a personal protective equipment device, the method comprising:

receiving an ambient sound stream;

parsing, using a model application engine, the ambient sound into a plurality of sound objects;

identifying one of the sound objects, using a sound analyzer;

retrieving a model from a model database based on the identified sound object;

processing the ambient sound by applying the retrieved model to the identified sound object to obtain a modified sound object and recombining the plurality of sound objects into a modified sound, wherein the modified sound includes the modified sound object instead of the identified sound object; and broadcasting the modified sound to a wearer of the personal protection device through a speaker of the personal protection device.

17. The method of claim 16, wherein the ambient sound is received through a microphone positioned on an exterior of the personal protection device.

18. The method of claim 16, wherein the method also comprises:

identifying a second sound object, using the sound analyzer;

retrieving a model from a model database based on the identified second sound object;

processing the identified second sound object into a second modified sound object; and recombining the first and second modified sound object into the modified sound.

19. The method of claim 16, and further comprising:

identifying one of the plurality of sound objects as an unknown sound object; and sending the unknown sound object to a second device for identification.

20. The method of claim 19, and further comprising applying a level dependent function to the unknown sound object and recombining it into the modified sound object.

* * * * *